(12) United States Patent
Lai et al.

(10) Patent No.: US 12,202,849 B2
(45) Date of Patent: Jan. 21, 2025

(54) CRYSTALLINE FORMS OF TENOFOVIR ALAFENAMIDE

(71) Applicant: Gilead Sciences, Inc., Foster City, CA (US)

(72) Inventors: Chiajen Lai, Livermore, CA (US); Bing Shi, Redwood City, CA (US); Robert G. Strickley, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/885,883

(22) Filed: Aug. 11, 2022

(65) Prior Publication Data

US 2023/0091736 A1 Mar. 23, 2023

Related U.S. Application Data

(60) Continuation of application No. 16/360,763, filed on Mar. 21, 2019, now Pat. No. 11,440,928, which is a division of application No. 15/882,784, filed on Jan. 29, 2018, now Pat. No. 10,287,307.

(60) Provisional application No. 62/452,428, filed on Jan. 31, 2017.

(51) Int. Cl.
| | |
|---|---|
| *C07F 9/6561* | (2006.01) |
| *A61K 9/00* | (2006.01) |
| *A61K 31/675* | (2006.01) |
| *A61K 45/06* | (2006.01) |

(52) U.S. Cl.
CPC ........ *C07F 9/65616* (2013.01); *A61K 9/0019* (2013.01); *A61K 31/675* (2013.01); *A61K 45/06* (2013.01); *C07B 2200/13* (2013.01)

(58) Field of Classification Search
CPC ... C07F 9/65616; A61K 31/675; A61K 45/06; A61K 9/0019; C07B 2200/13
See application file for complete search history.

(56) References Cited

U.S. PATENT DOCUMENTS

| | | |
|---|---|---|
| 9,908,908 B2 | 3/2018 | Zhang et al. |
| 10,287,307 B2 | 5/2019 | Lai et al. |
| 11,440,928 B2 | 9/2022 | Lai et al. |
| 2012/0149708 A1 | 6/2012 | Kashanchi |
| 2013/0065856 A1 | 3/2013 | Liu et al. |
| 2016/0237073 A1 | 8/2016 | Hamblin et al. |
| 2017/0050932 A1 | 2/2017 | Lynch et al. |

FOREIGN PATENT DOCUMENTS

| | | |
|---|---|---|
| CN | 104558036 A | 4/2015 |
| CN | 105085571 A | 11/2015 |
| EP | 0903341 A1 | 3/1999 |
| KR | 1020150025993 A1 | 3/2015 |

(Continued)

OTHER PUBLICATIONS

Anderson, B. et. al. (1996) "Preparation of Water-Soluble Compounds Through Salt Formation" *The Practice of Medicinal Chemistry* 740-754.

(Continued)

*Primary Examiner* — Valerie Rodriguez-Garcia

(57) ABSTRACT

The present invention relates to novel crystalline forms of salts and/or co-crystals of tenofovir alafenamide, the pharmaceutical formulations, and the therapeutic uses thereof in treating viral infections.

22 Claims, 18 Drawing Sheets

XRPD pattern for Tenofovir Alafenamide Napsylate Form 1

(56) References Cited

FOREIGN PATENT DOCUMENTS

| WO | WO-2002/008241 A2 | 1/2002 |
|---|---|---|
| WO | WO-2004/087720 A1 | 10/2004 |
| WO | WO-2010/101967 A2 | 9/2010 |
| WO | WO-2012/030927 A2 | 3/2012 |
| WO | WO-2012/032067 A1 | 3/2012 |
| WO | WO-2013/025788 A1 | 2/2013 |
| WO | WO-2013/095684 A1 | 6/2013 |
| WO | WO-2014/172243 A1 | 10/2014 |
| WO | WO-2014/195724 A1 | 12/2014 |
| WO | WO-2015/002434 A1 | 1/2015 |
| WO | WO-2015/040640 A2 | 3/2015 |
| WO | WO-2015/107451 A2 | 7/2015 |
| WO | WO2015/176602 | * 11/2015 |
| WO | WO-2015/176602 A1 | 11/2015 |
| WO | WO-2016/081940 A1 | 5/2016 |
| WO | WO-2016/192692 A1 | 12/2016 |
| WO | WO 2016/205141 | * 12/2016 |
| WO | WO-2016/205141 A1 | 12/2016 |
| WO | WO-2017/004012 A1 | 1/2017 |
| WO | WO-2018/144390 A1 | 8/2018 |

OTHER PUBLICATIONS

Bastin et al., (Organic Process Research & Development 200, 4, 427-435).
Chrzanowski et al., "The preparation and evaluation of salt forms of linogliride with reducedsolubilities as candidates for extended release," Drug Development and Industrial Pharmacy (2017) 43:3 pp. 421-431.
Communication pursuant to Rules 161(1) and 162 EPC dated Oct. 11, 2019 for European Appl. No. 18705239.4.
Elder, D. et al. (2010) "The Utility of Sulfonate Salts in Drug Development" *Journal of Pharmaceutical Sciences* 99(7):2948-2961.
Exam Report dated Jan. 27, 2022 for Australian Application No. 2021200857.
Exam Report dated Mar. 11, 2022 for European Appl. No. 18705239.4.
Examination Report dated Feb. 18, 2020 for Australian Appl. No. 2018216738.
Examination Report dated Mar. 19, 2020 for Indian Appl. No. 201917032116.
Final Rejection dated Jun. 10, 2021 for Korean Appl. No. 10-2019-7025206.
International Preliminary Report on Patentability Issued 2019-08-06 for PCT App No. PCT/US2018/015770; 7pgs.
International Search Report and Written Opinion for PCT/US2018/015770, dated Mar. 23, 2018, 12 pages.
Kojima, T. (2008) "Effective Solid Form Selection for the Pharmaceutical Development" *Journal of Pharmaceucitcal Science and Technology*, Japan 68(5):344-349.
Li, C.J. et al. (2017) "In vitro and in vivo release of dinalbuphine sebacate extended release formulation: Effect of the oil ratio on drug release" *Int J Pharm* 531(1):306-12.
Notice of Preliminary Rejection dated Feb. 23, 2021 for Korean Appl. No. 10-2019-7025206.
Office Action dated Dec. 10, 2018 for Taiwanese App. No. 107102293, 6pgs.
Office Action dated Aug. 12, 2019 for Taiwanese App No. 107102293; 3pgs.
Office Action dated Jun. 29, 2020 for Canadian Appl. No. 3049028.
Office Action dated Aug. 25, 2020 for Japanese Appl. No, 2019-541123.
Office Action dated Apr. 28, 2021 for Japanese Appl. No. 2019-541123.
Office Action dated May 5, 2021 for Canadian Appl. No. 3049028.
Office Action dated May 26, 2021 for Chinese Appl. No. 201880009292.1.
Office Action dated Feb. 23, 2021 for Korean Appl. No. 10-2021-7034440.
Office Action dated Jan. 5, 2022 for Korean Appl. No. 10-2021-7012232.
Office Action dated Jan. 20, 2022 for Taiwanese Appl. No. 109143905.
Office Action dated Jan. 28, 2022 for Argentinian Appl. No. 20180100144.
Office Action dated Feb. 1, 2022 for Japanese Application No. 2020-195169.
Office Action dated Feb. 15, 2022 for Chinese Appl. No. 201880009292.1.
Patel, A. et al. (2009) "Pharmaceutical salts: A formulation trick or a clinical conundrum?" *British Journal of Cardiology* 16(6):281-6.
Sarma, B. et al. (2011) "Solid forms of pharmaceuticals: Polymoprhs, salts and cocrystals" *Korean Journal of Chemical Engineering* 28(2):315-322.
Second Final Rejection dated Aug. 20, 2021 for Korean Appl. No. 10-2019-7025206.
Stahl et al. (eds., Handbook of Pharmaceutical Salts. Properties, Selection and Use (Wiley-VCH, 2008), pp. 265-327).
Stahl, P.H. et al. (2008) Handbook of Pharmaceutical Salts: Properties, Selection, and Use: 1-7, 103-104, 109-110, 120, 154-157, 163, 164-170, 192-220.
Swarbrick et al. (Encyclopedia of Pharmaceutical Technology 13 (Marcel Dekker, NY 1996) pp. 453-499).
Third Party Observation dated May 31, 2019 for PCT Appl. No. PCT/US2018/015770.
Verbeeck, R.K. et al. (2006) "Generic Substitution: The Use of Medicinal Products Containing Different Salts and Implications for Safety and Efficacy" *European Journal of Pharmaceutical Sciences* (28):1-6.
Office Action dated Aug. 1, 2022 for Chinese Application No. 201880009292.1.
Office Action dated Aug. 5, 2022 for Korean Application No. 10-2021-7012232.
Office Action dated Aug. 5, 2022 for Korean Application No. 10-2021-7034440.
Pre-Appeal Examination Report dated Nov. 29, 2022 for Japanese Application No. 2019- 541123.
Office Action dated Jan. 5, 2023 for Korean Application No. 10-2021-7034440.
Gunawardana et al. (2015) "Antimicrob Agents Chemother", 59(7): 3913-3919.
Office Action dated Feb. 15, 2023 for Korean Appl. No. 10-2021-7012232, 7 pages.
Office Action dated Feb. 3, 2023 for Taiwanese Appl. No. 111140896, 11 pages.
Examination Report dated Oct. 12, 2023 for Australian Appl. No. 2022283687, 3 pages.
Notice of Allowance dated Mar. 11, 2019 for U.S. Appl. No. 15/882,784.
Non-Final Office Action dated Mar. 10, 2020 for U.S. Appl. No. 16/360,763.
Notice of Allowance dated Jul. 2, 2020 for U.S. Appl. No. 16/360,763.
Non-Final Office Action dated Nov. 23, 2020 for U.S. Appl. No. 16/360,763.
Final Office Action dated Apr. 20, 2021 for U.S. Appl. No. 16/360,763.
Non-Final Office Action dated Nov. 9, 2021 for U.S. Appl. No. 16/360,763.
Examination Report dated Nov. 26, 2021 for Indian Appl. No. 202018054920.
Final Office Action dated Mar. 28, 2022 for Japanese Appl. No. 2019-541123.
Notice of Allowance dated May 13, 2022 for U.S. Appl. No. 16/360,763.
Office Action dated Oct. 4, 2022 for Japanese Appl. No. 2021-176746, 3 pages.
Final Office Action dated Nov. 16, 2022 for Japanese Application No. 2020-195169.
Notice of Opposition dated Jan. 10, 2024 for Indian Appl. No. 202018054920.
Examination Report dated Jan. 29, 2024 for Canadian Appl. No. 3168042, 4 pages.

(56) References Cited

OTHER PUBLICATIONS

Pre-Grant Hearing Notice dated Apr. 16, 2024 for Indian Appl. No. 202018054920.
Office Action dated May 10, 2024 for Taiwanese Appl. No. 112137480.
Office Action dated May 31, 2024 for Chinese Appl. No. 202211484773.2.
Notice of Acceptance dated Aug. 22, 2024 for AU Appl. No. 2022283687.
Extended European Search Report dated Oct. 8, 2024 for EP Appl. No. 24173808.7.
Savjani, K et al. (2012) "Drug Solubility: Importance and Enhancement Techniques", ISRN Pharm; 2012:195727, 10 pages.

* cited by examiner

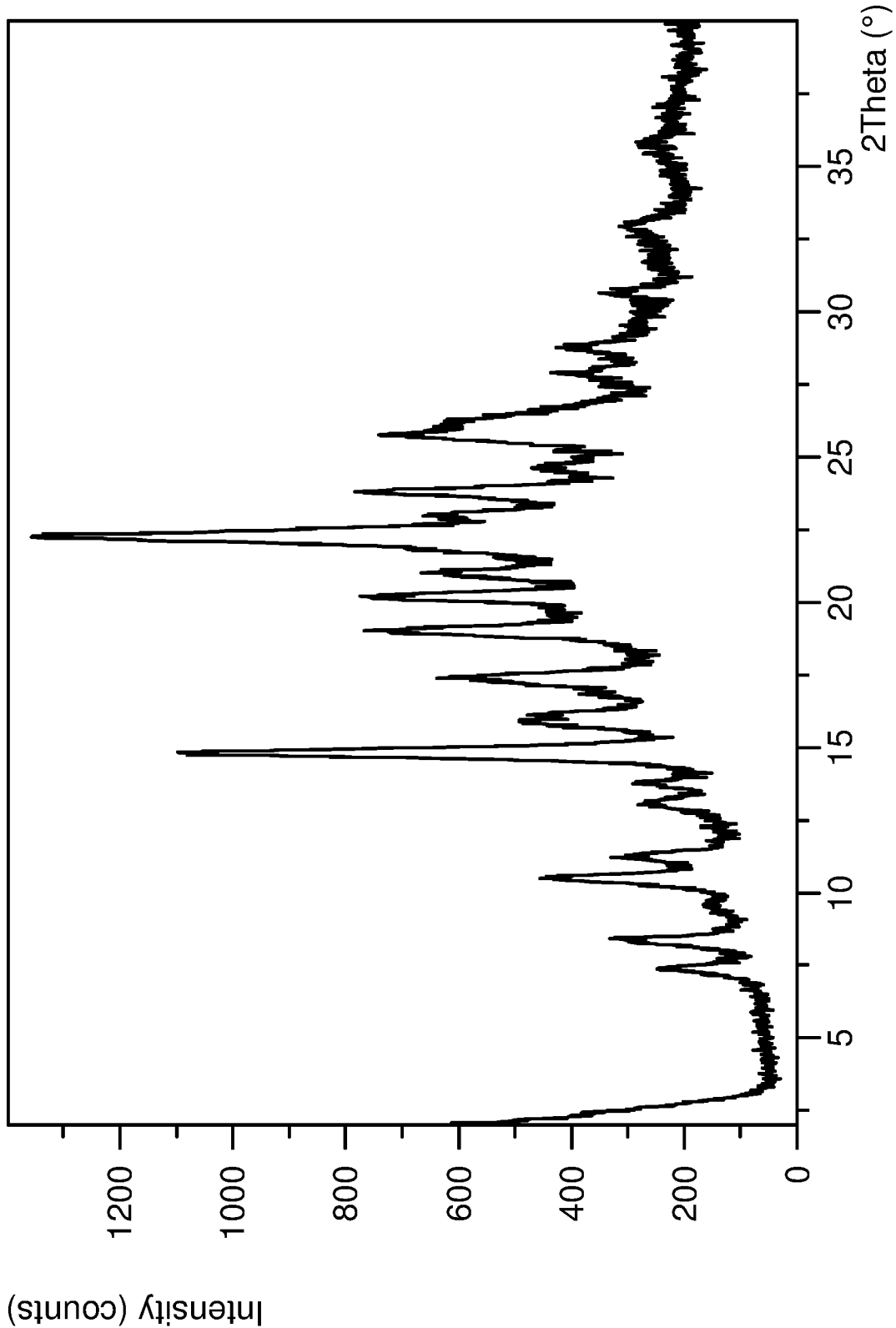
FIG. 1: XRPD pattern for Tenofovir Alafenamide Hemipamoate Form I

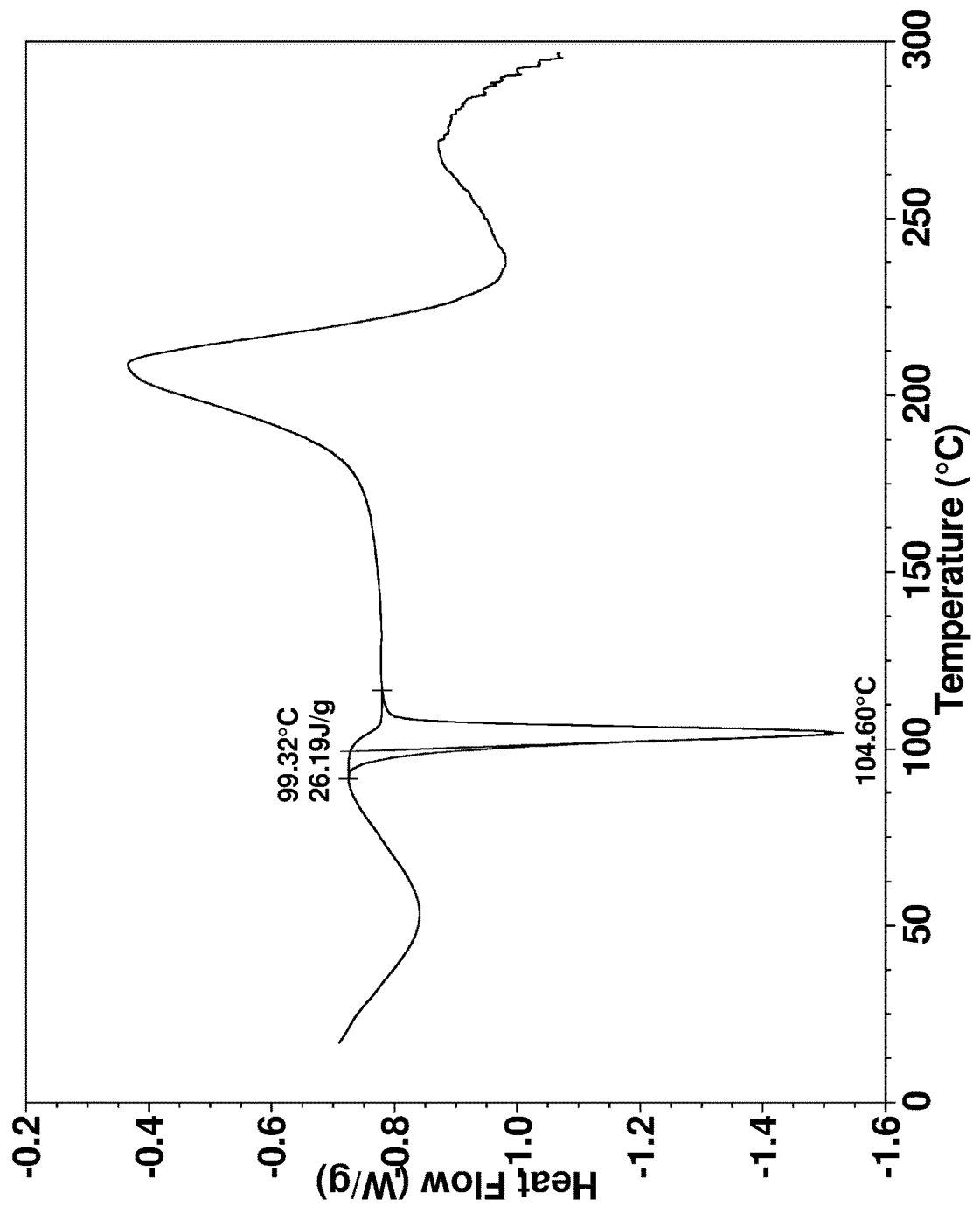
FIG. 2: DSC for Tenofovir Alafenamide Hemipamoate Form I

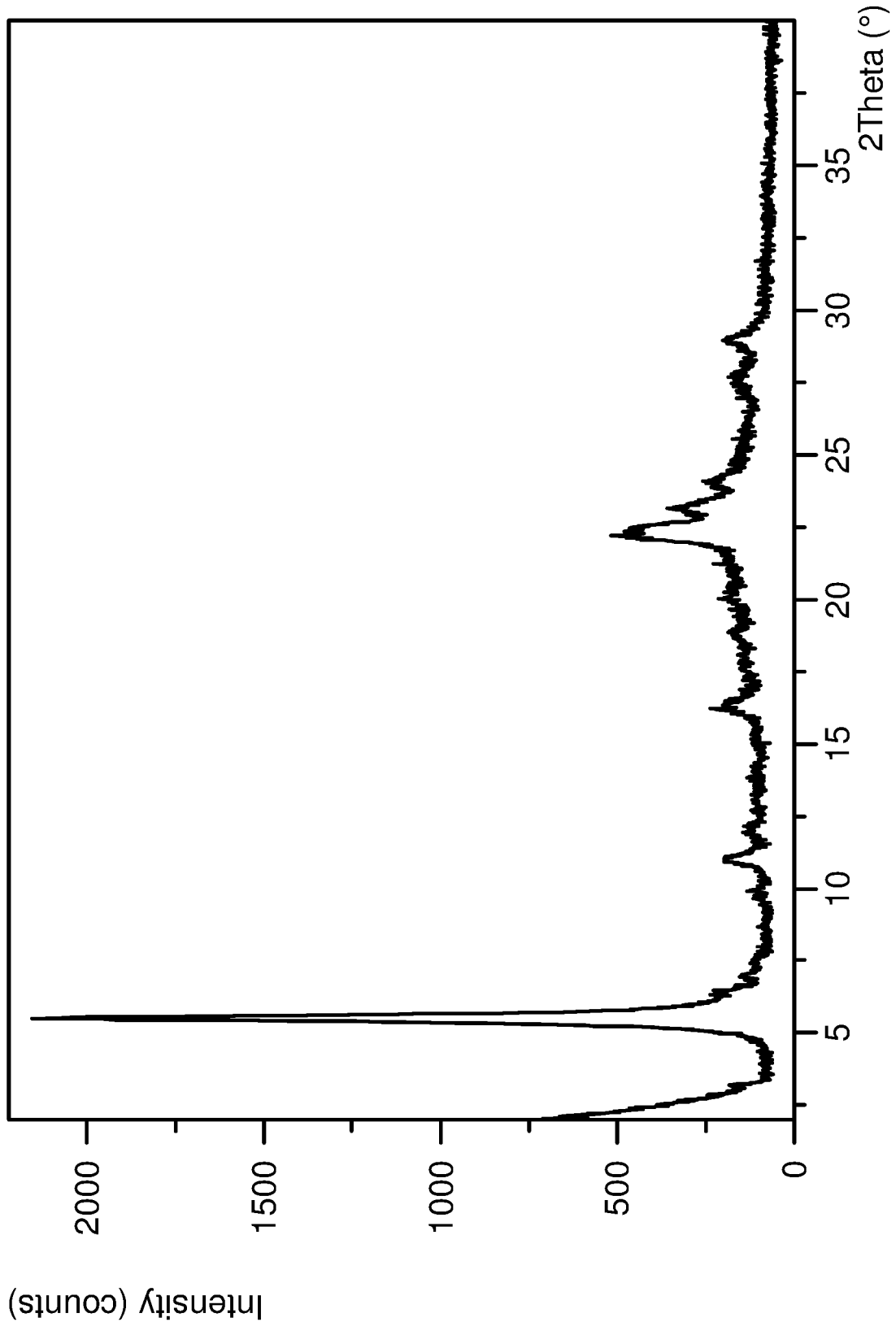
FIG. 3: XRPD for Tenofovir Alafenamide Hemipamoate Form II

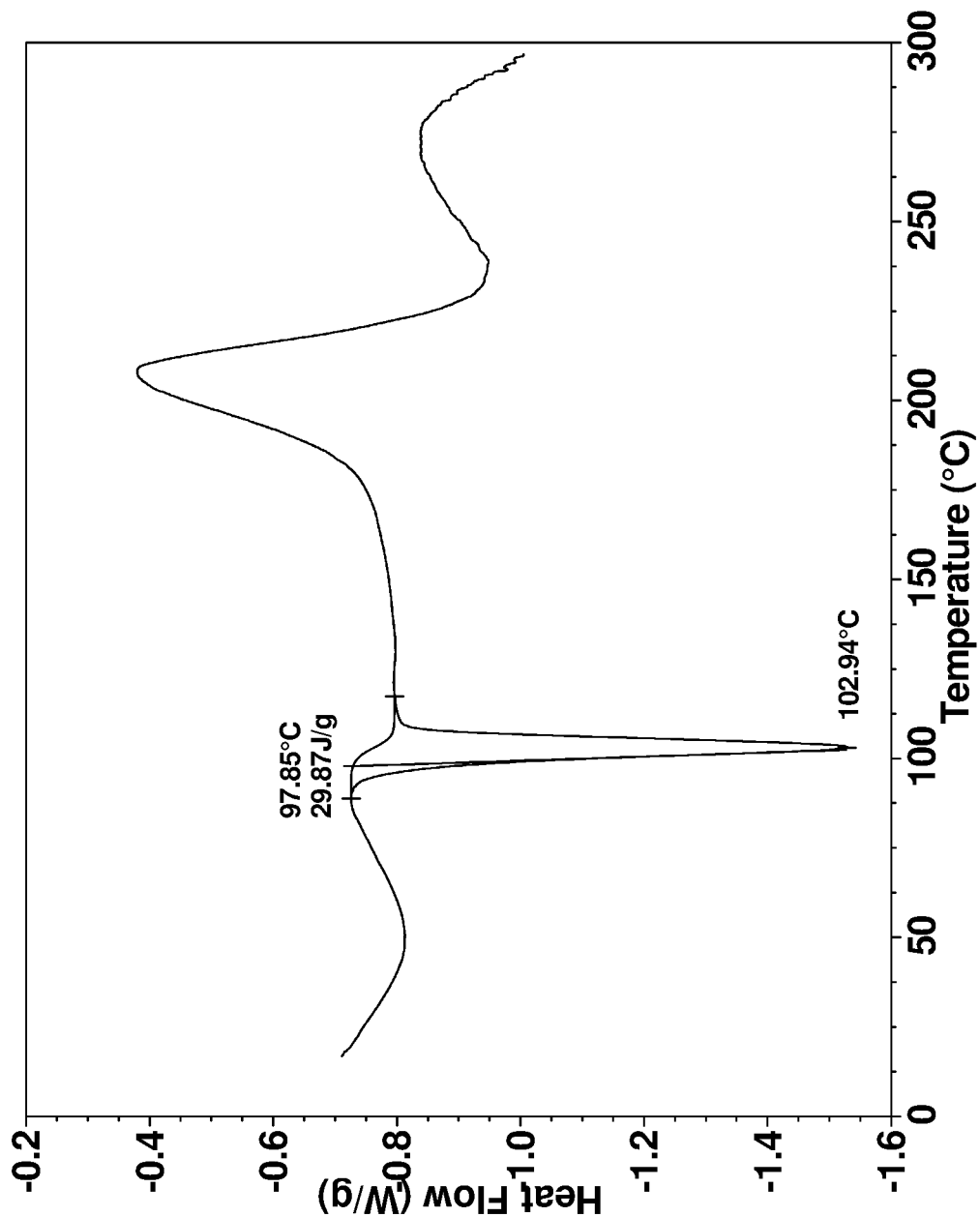
FIG. 4: DSC for Tenofovir Alafenamide Hemipamoate Form II

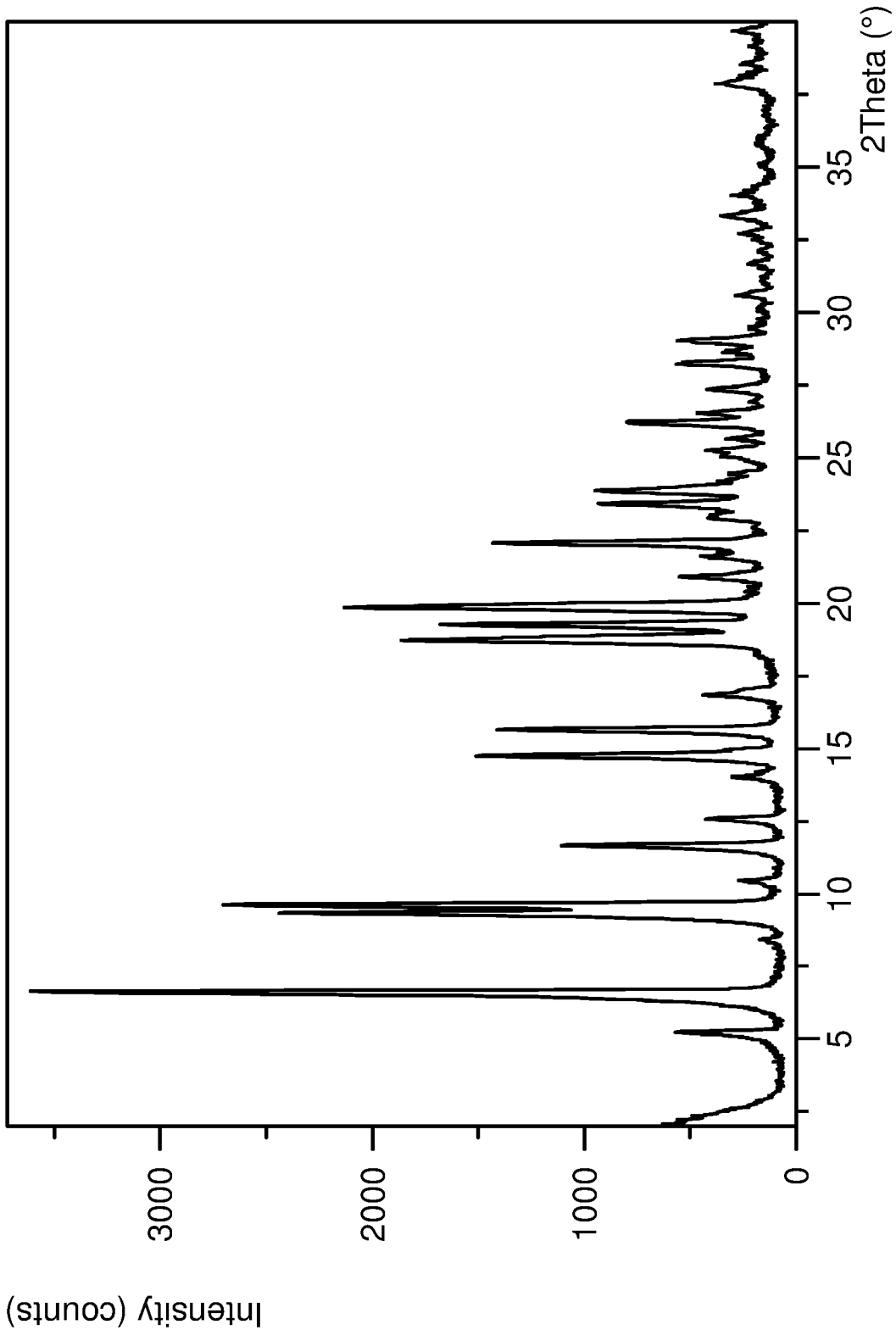
FIG. 5: XRPD pattern for Tenofovir Alafenamide Sebacate Form I

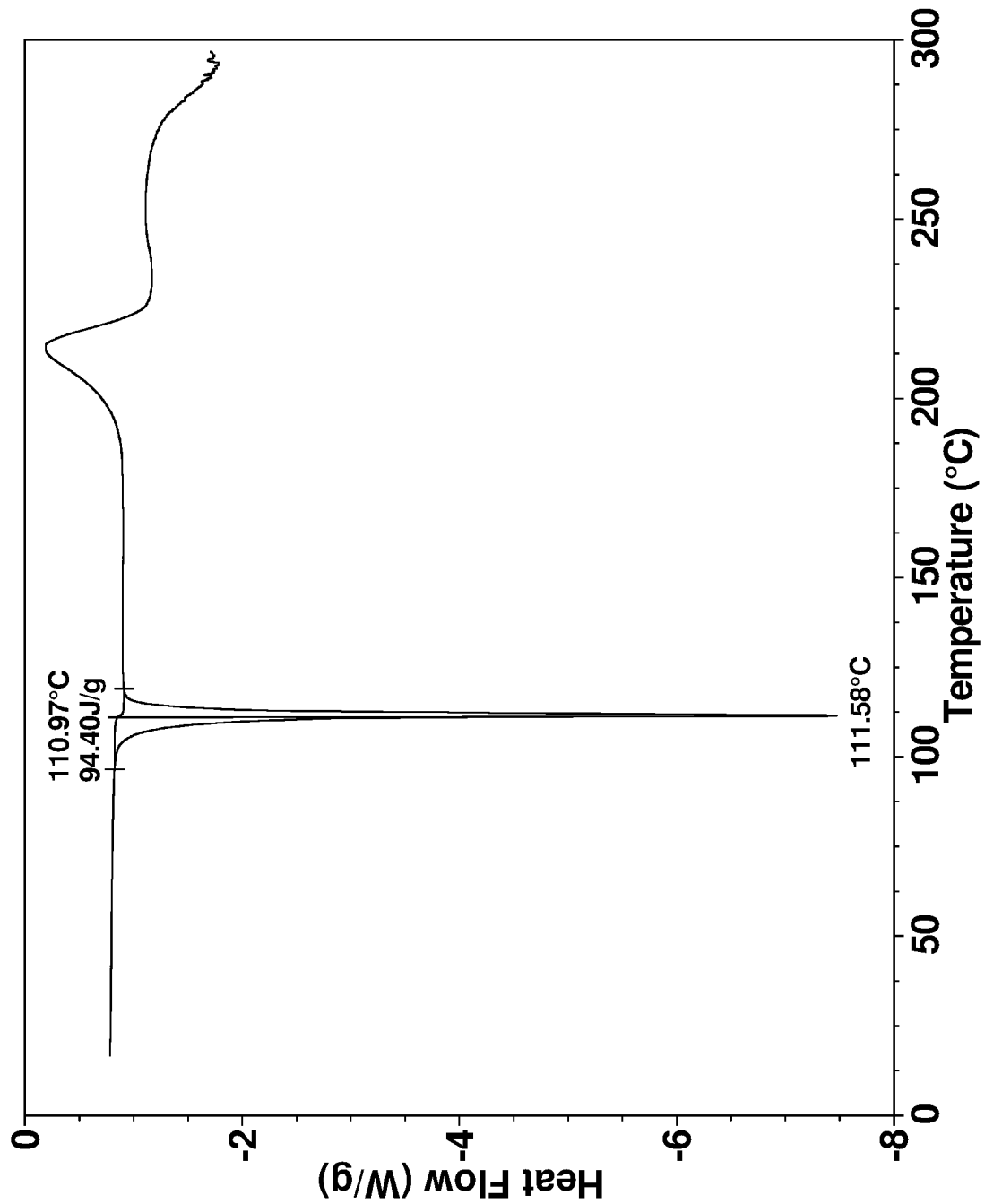
FIG. 6: DSC for Tenofovir Alafenamide Sebacate Form I

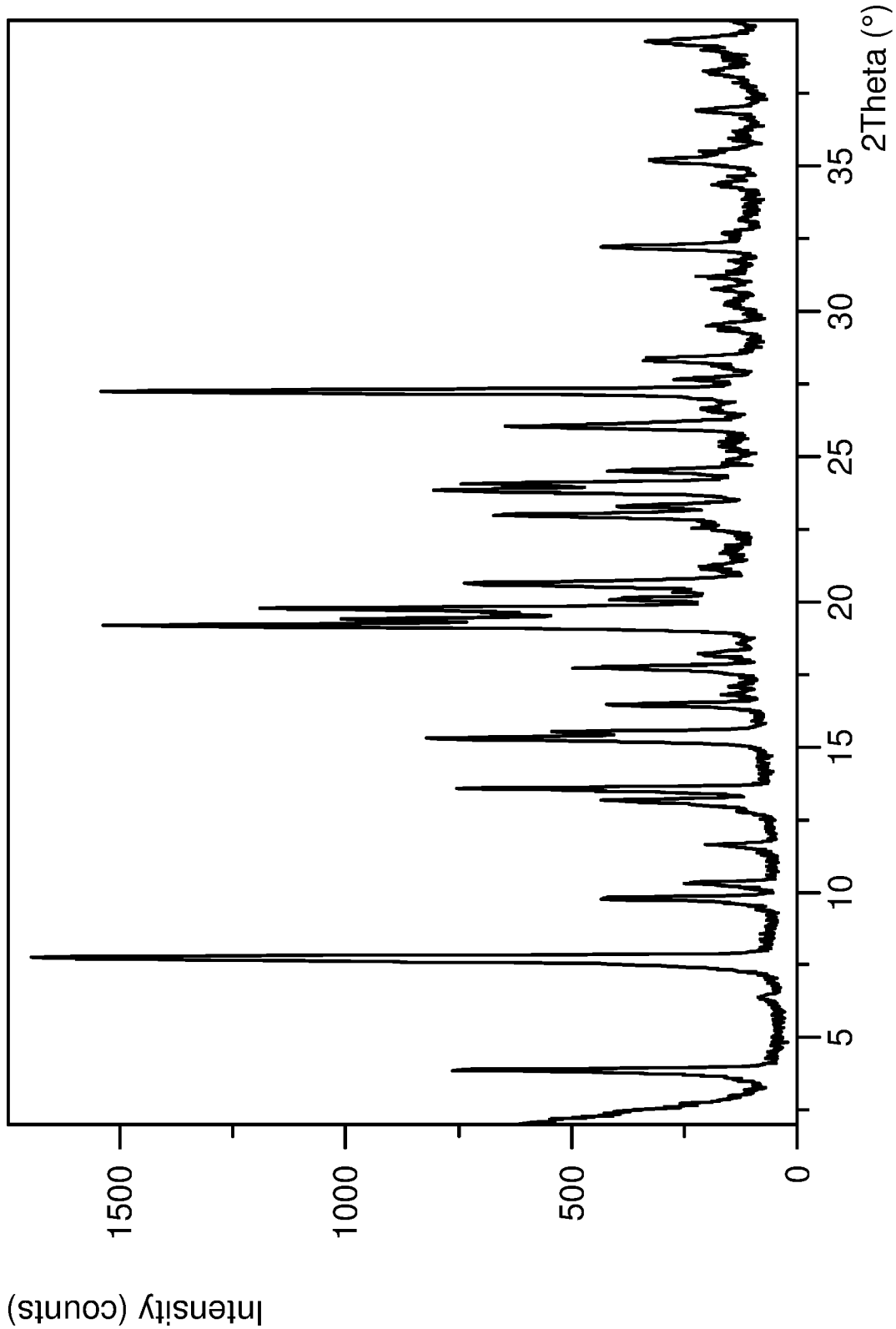
FIG. 7: XRPD pattern for Tenofovir Alafenamide Napsylate Form I

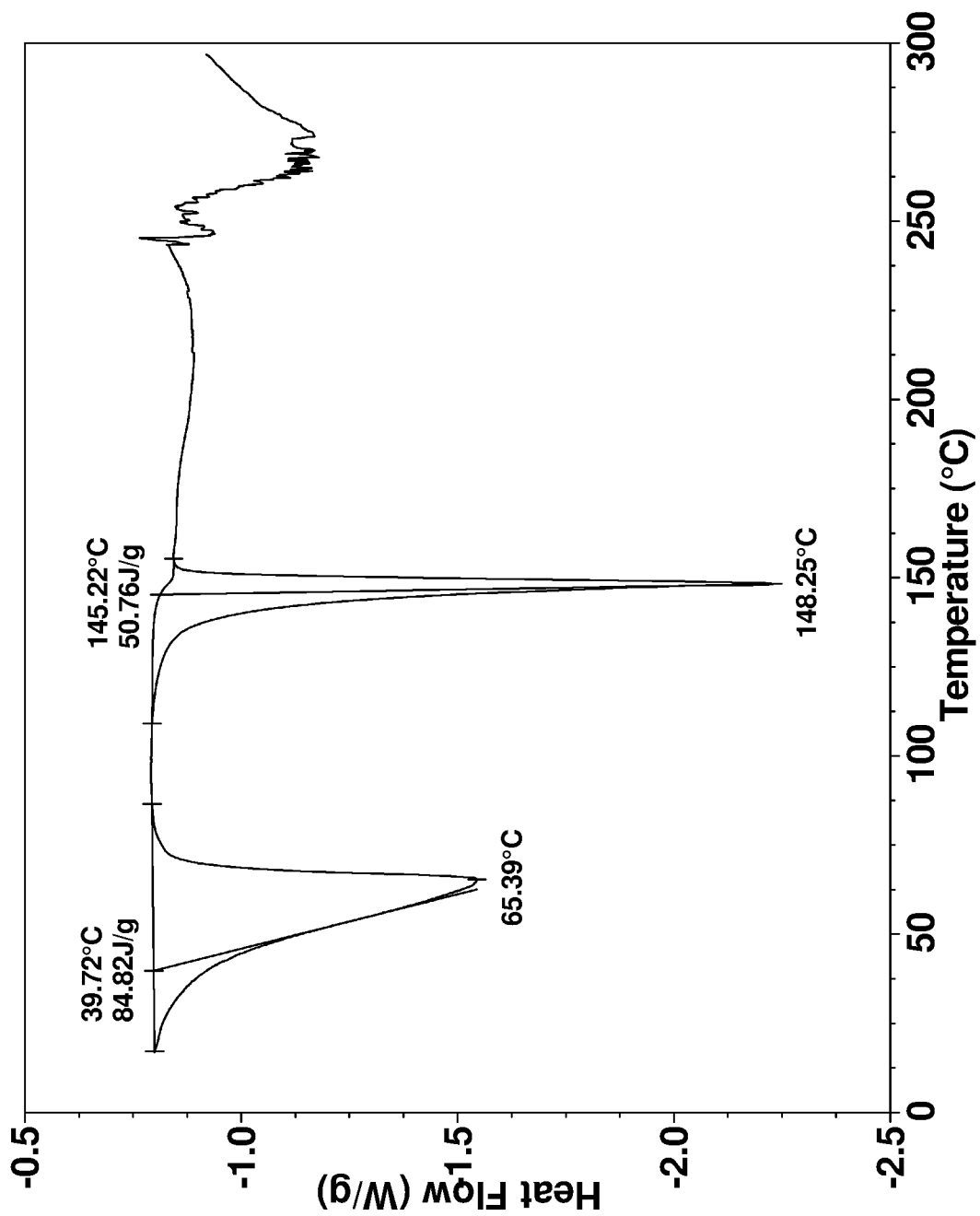
FIG. 8: DSC for Tenofovir Alafenamide Napsylate Form I

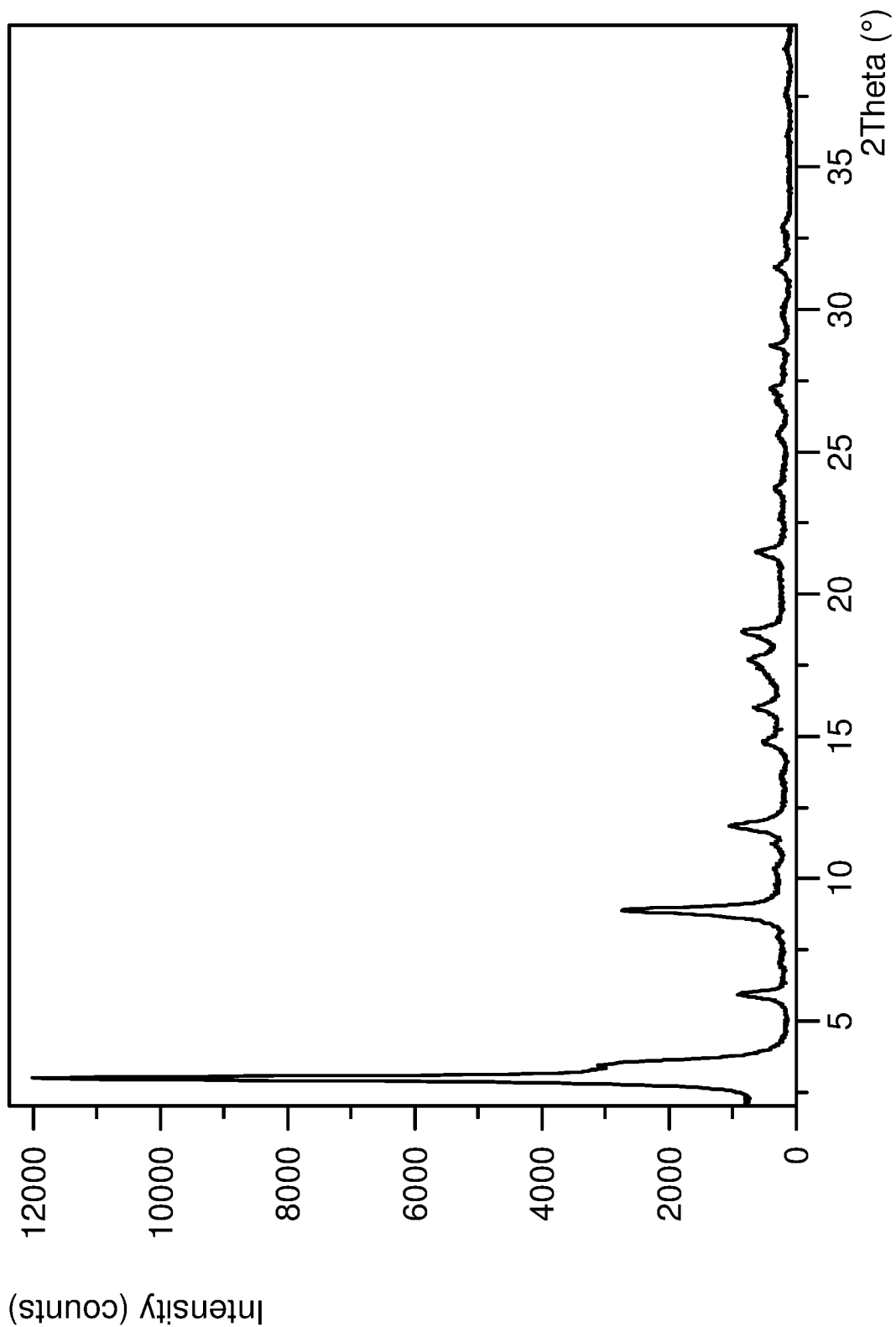
FIG. 9: XRPD pattern for Tenofovir Alafenamide Orotate Form I

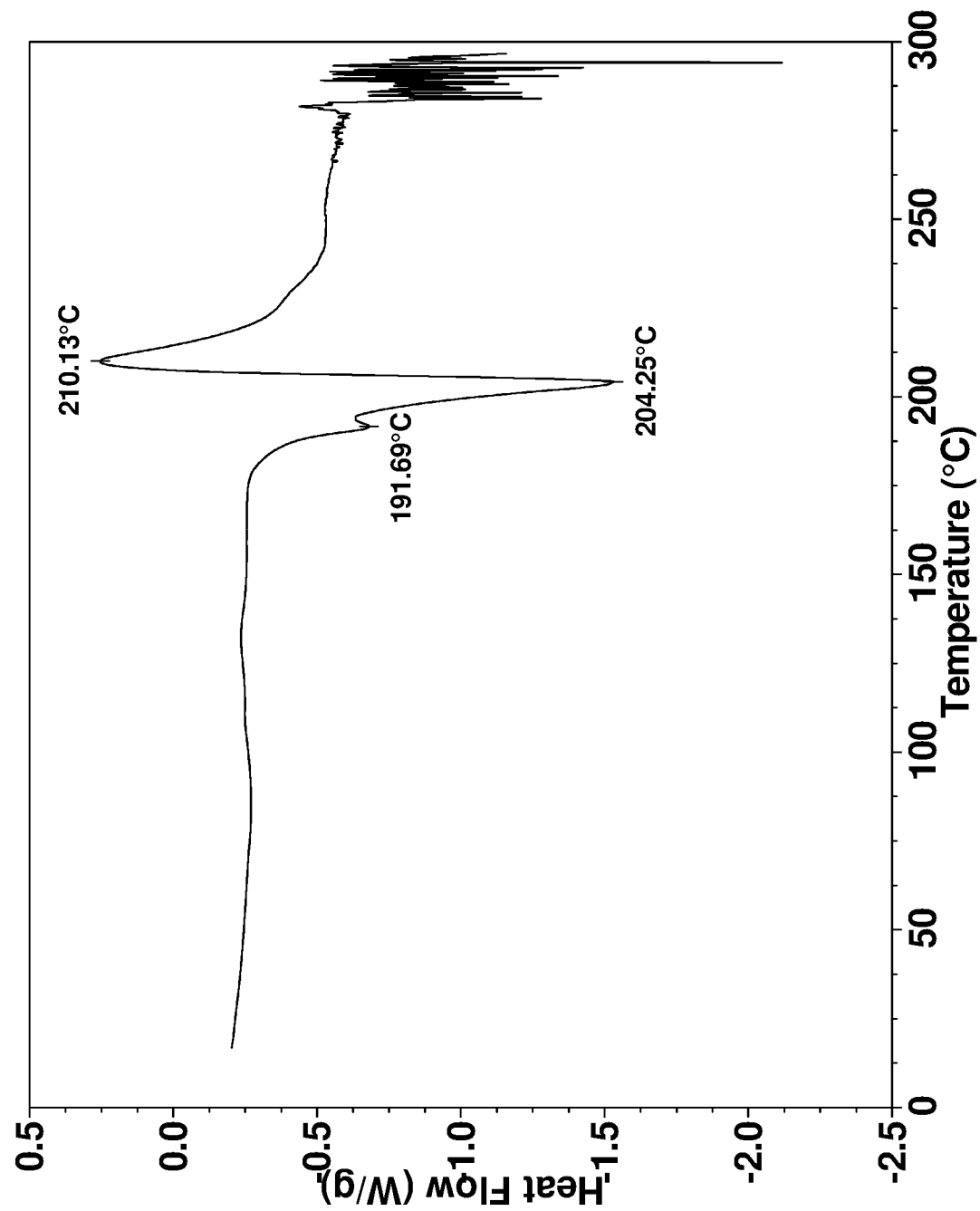
FIG. 10: DSC for Tenofovir Alafenamide Orotate Form I

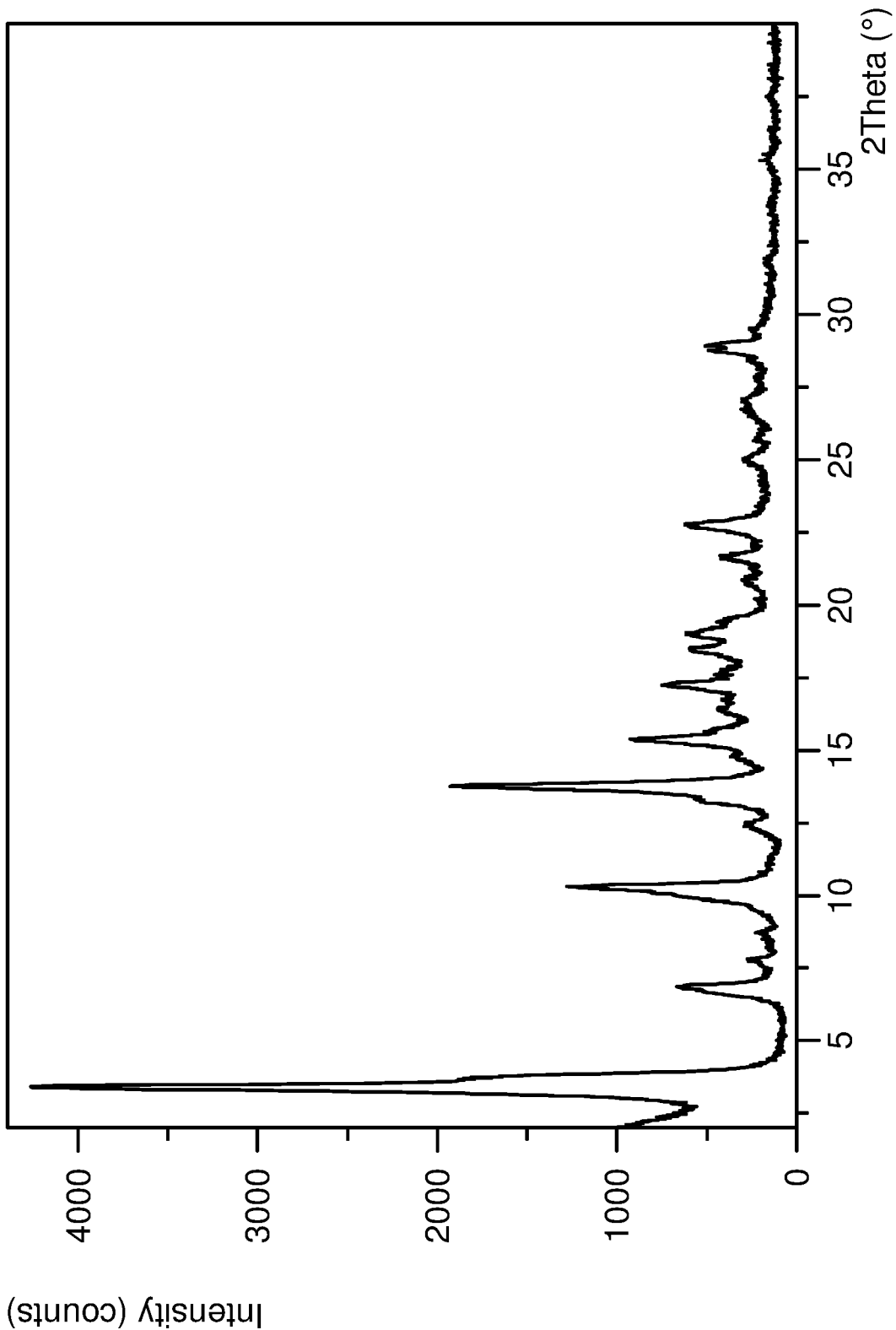
FIG. 11: XRPD pattern for Tenofovir Alafenamide Orotate Form II

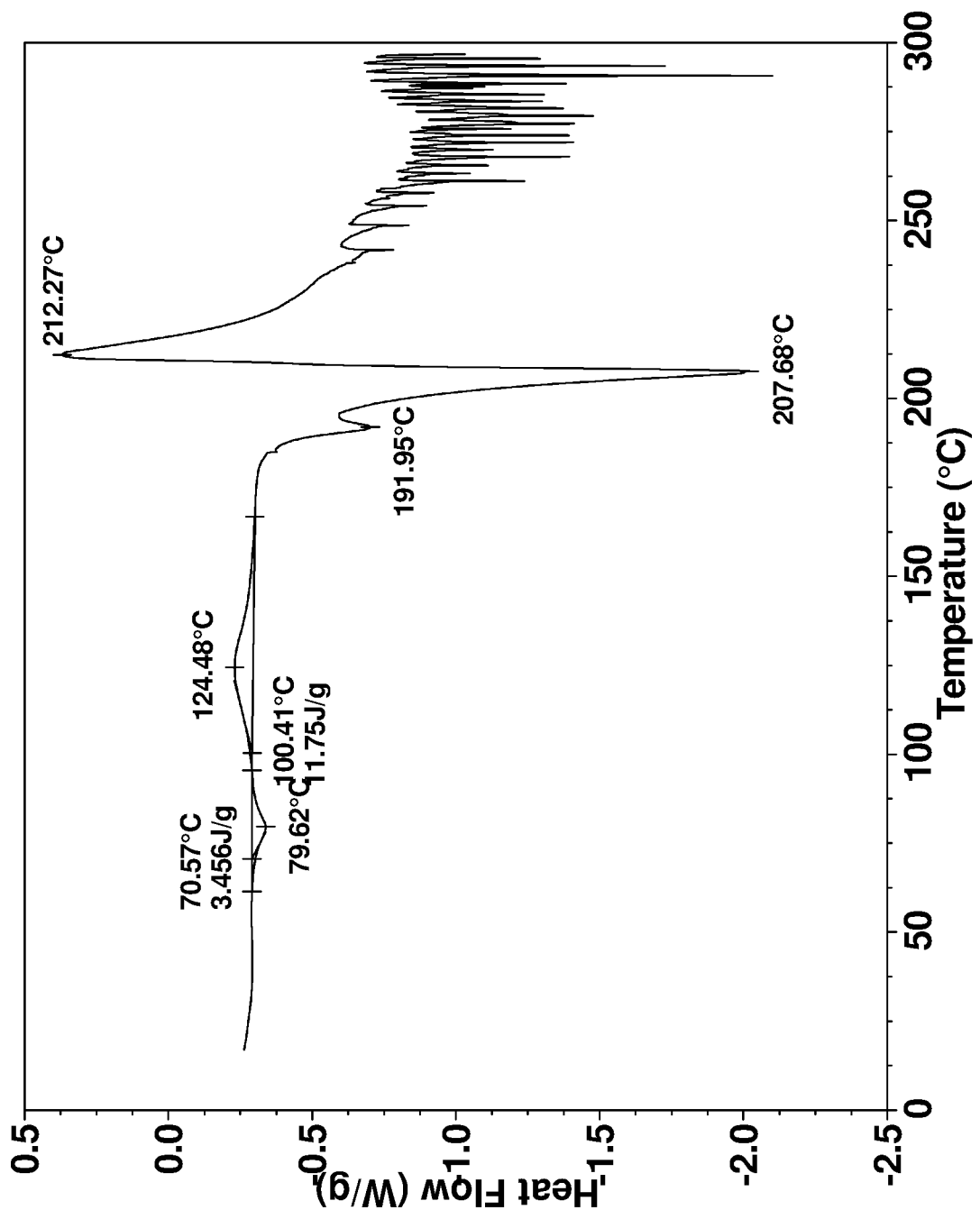
FIG. 12: DSC for Tenofovir Alafenamide Orotate Form II

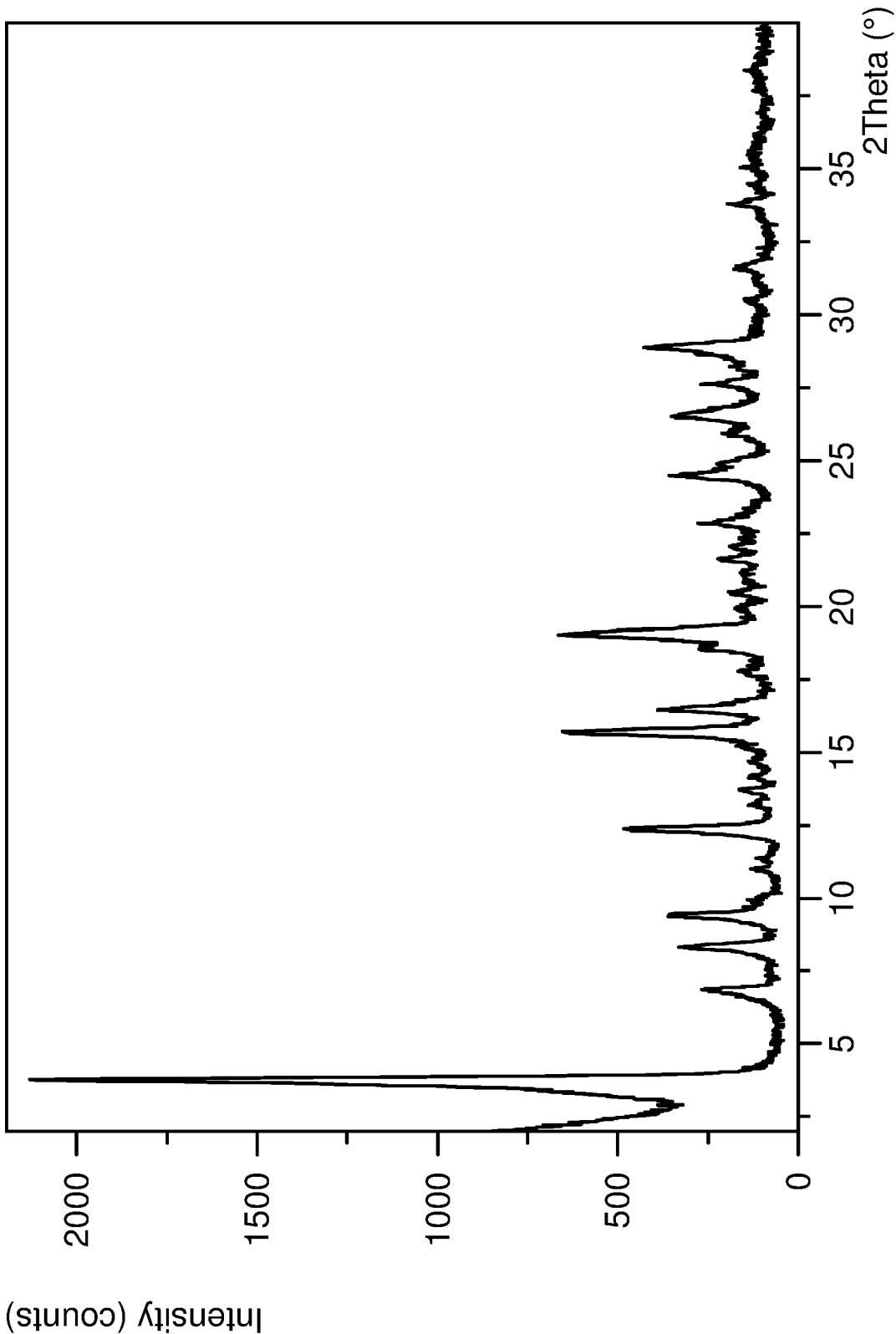
FIG. 13: XRPD pattern for Tenofovir Alafenamide Orotate Form III

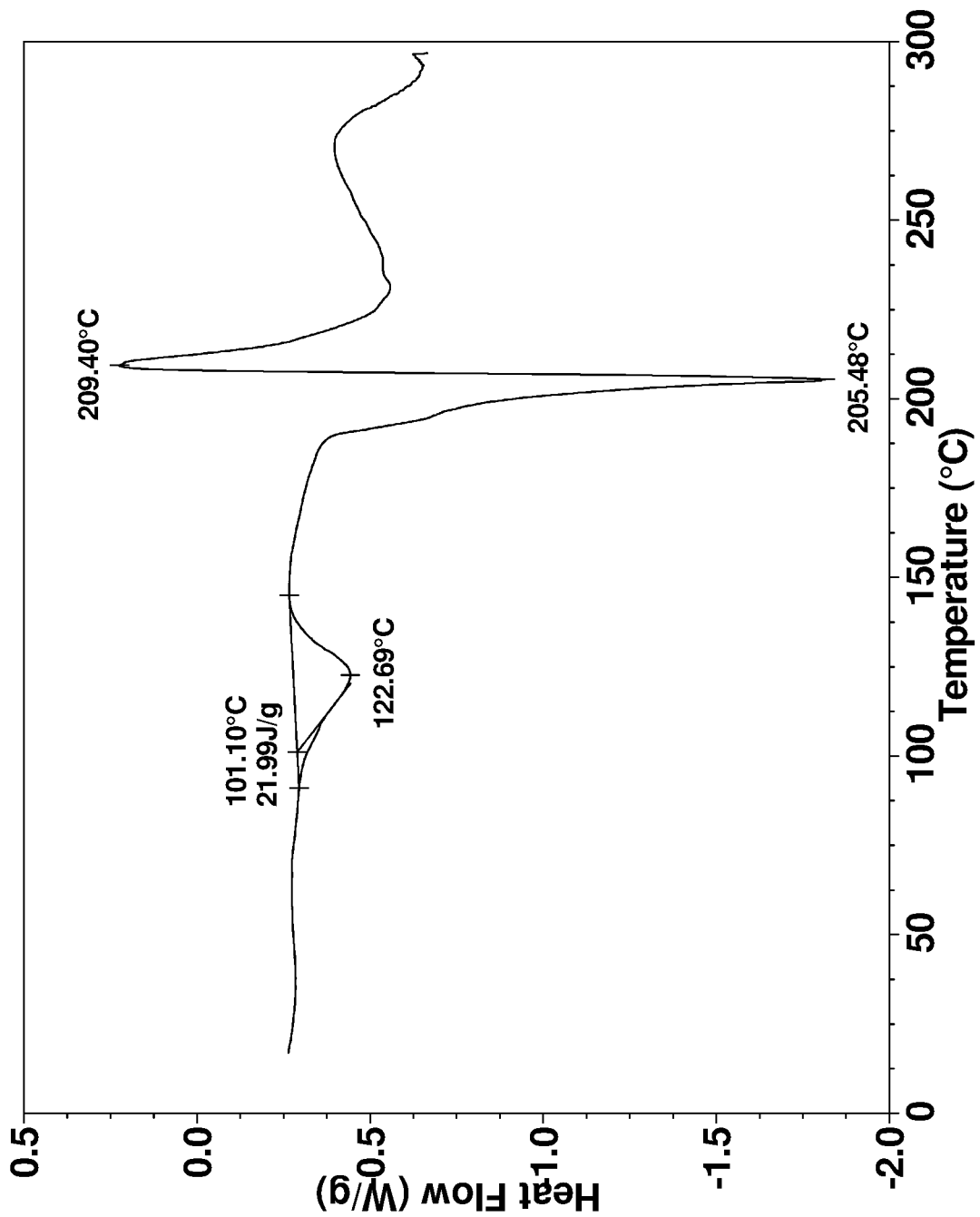
FIG. 14: DSC for Tenofovir Alafenamide Orotate Form III

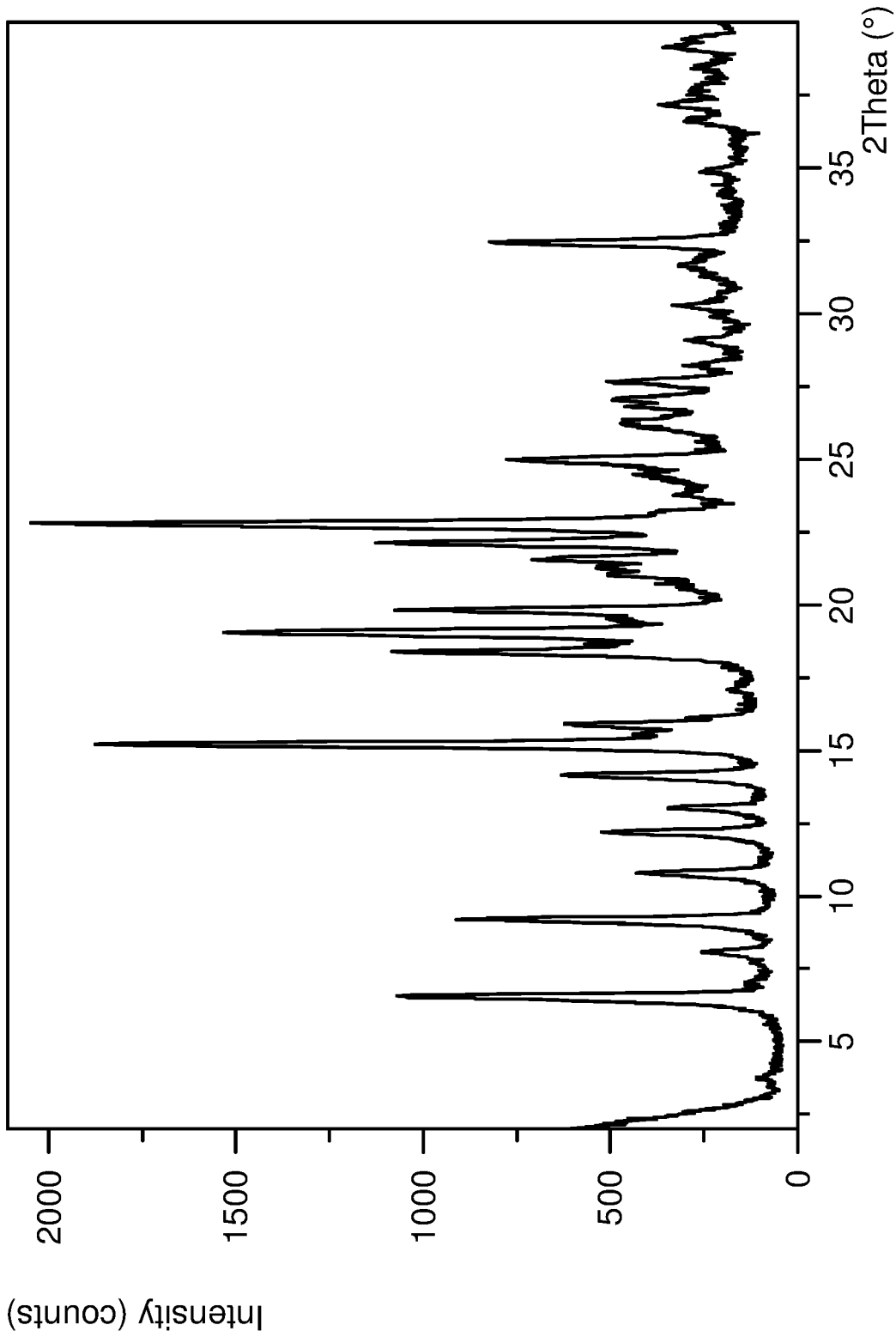
FIG. 15: XRPD pattern for Tenofovir Alafenamide Vanillate

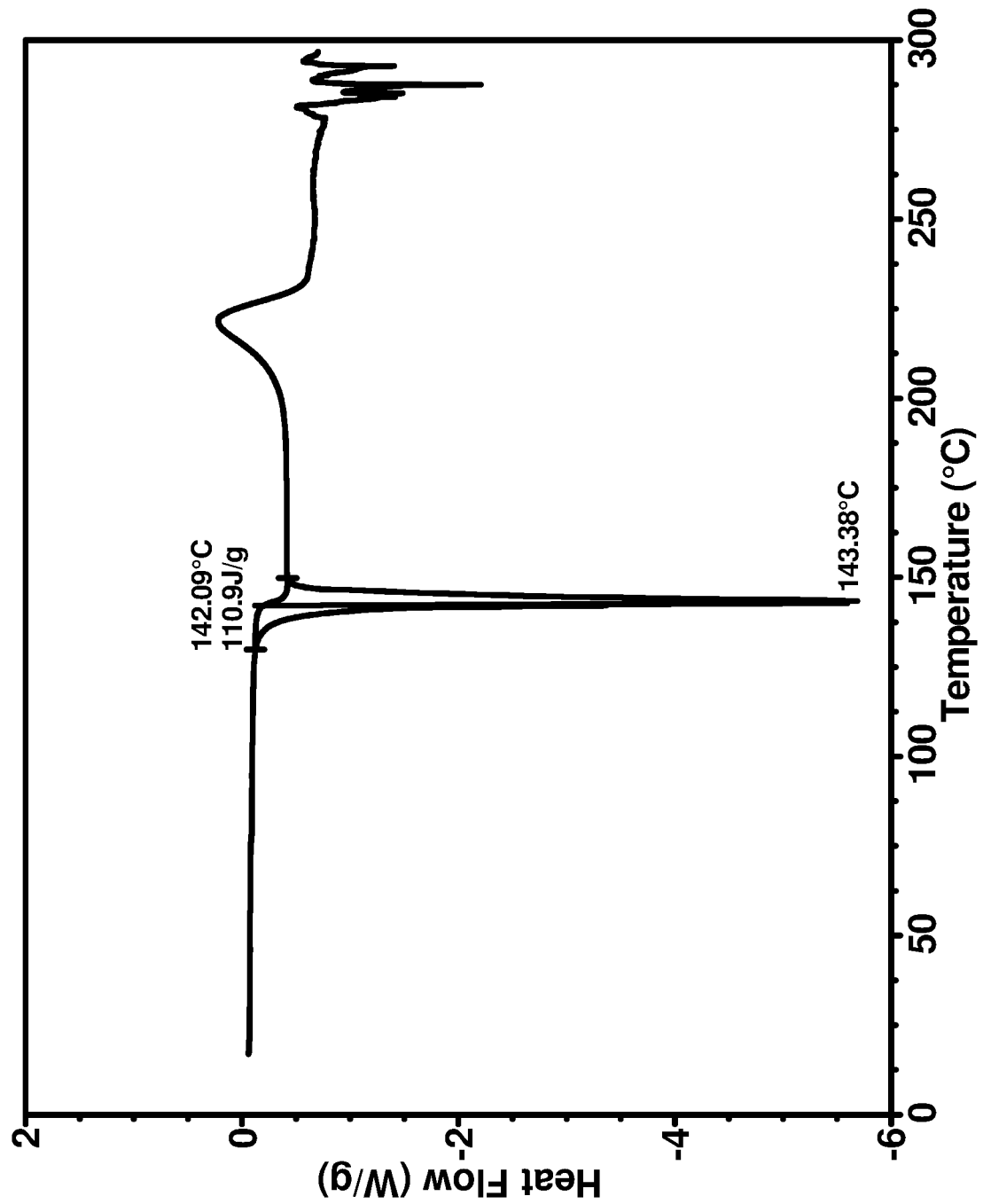
FIG. 16: DSC for Tenofovir Alafenamide Vanillate

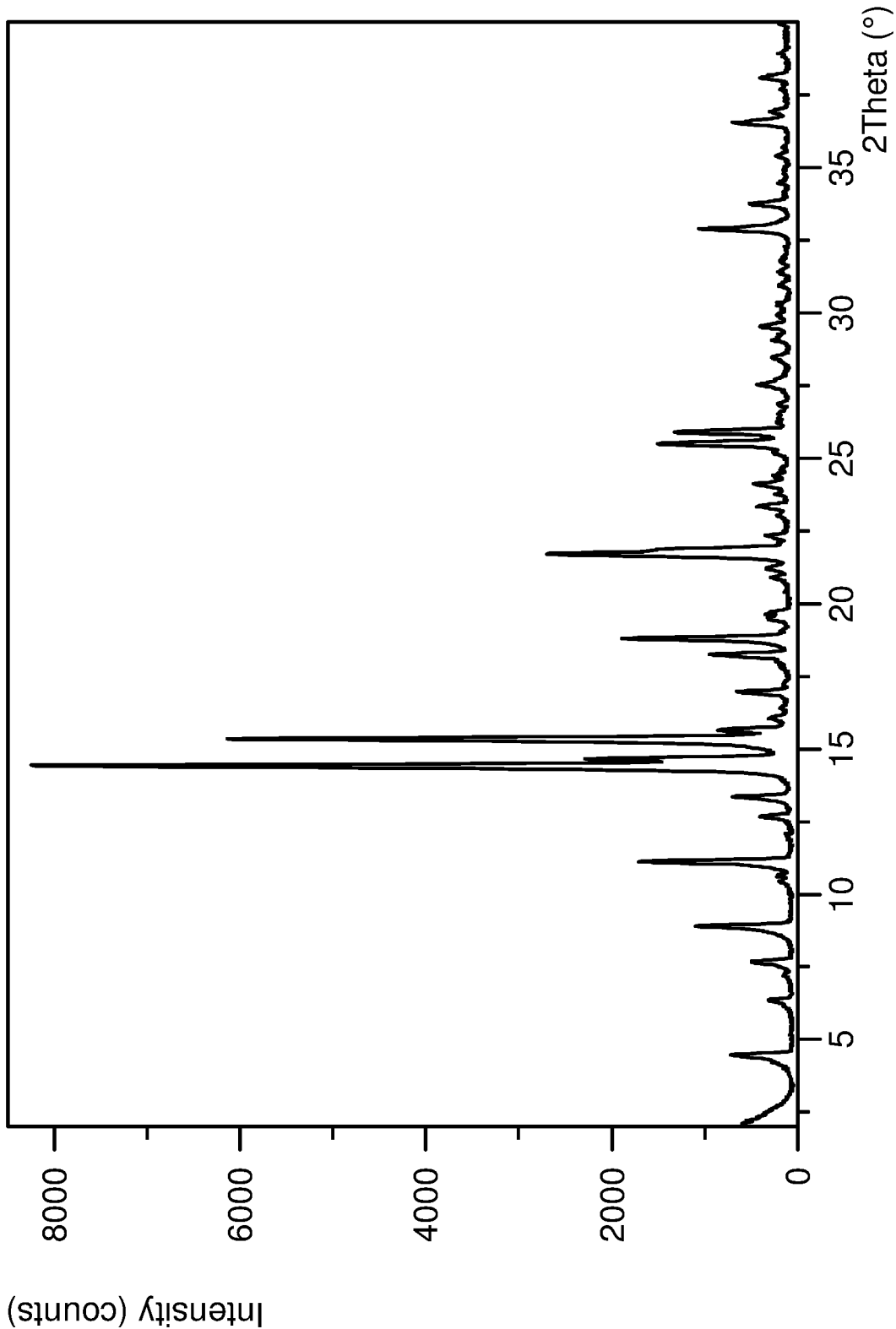
FIG. 17: XRPD pattern for Tenofovir Alafenamide Bis-Xinafoate

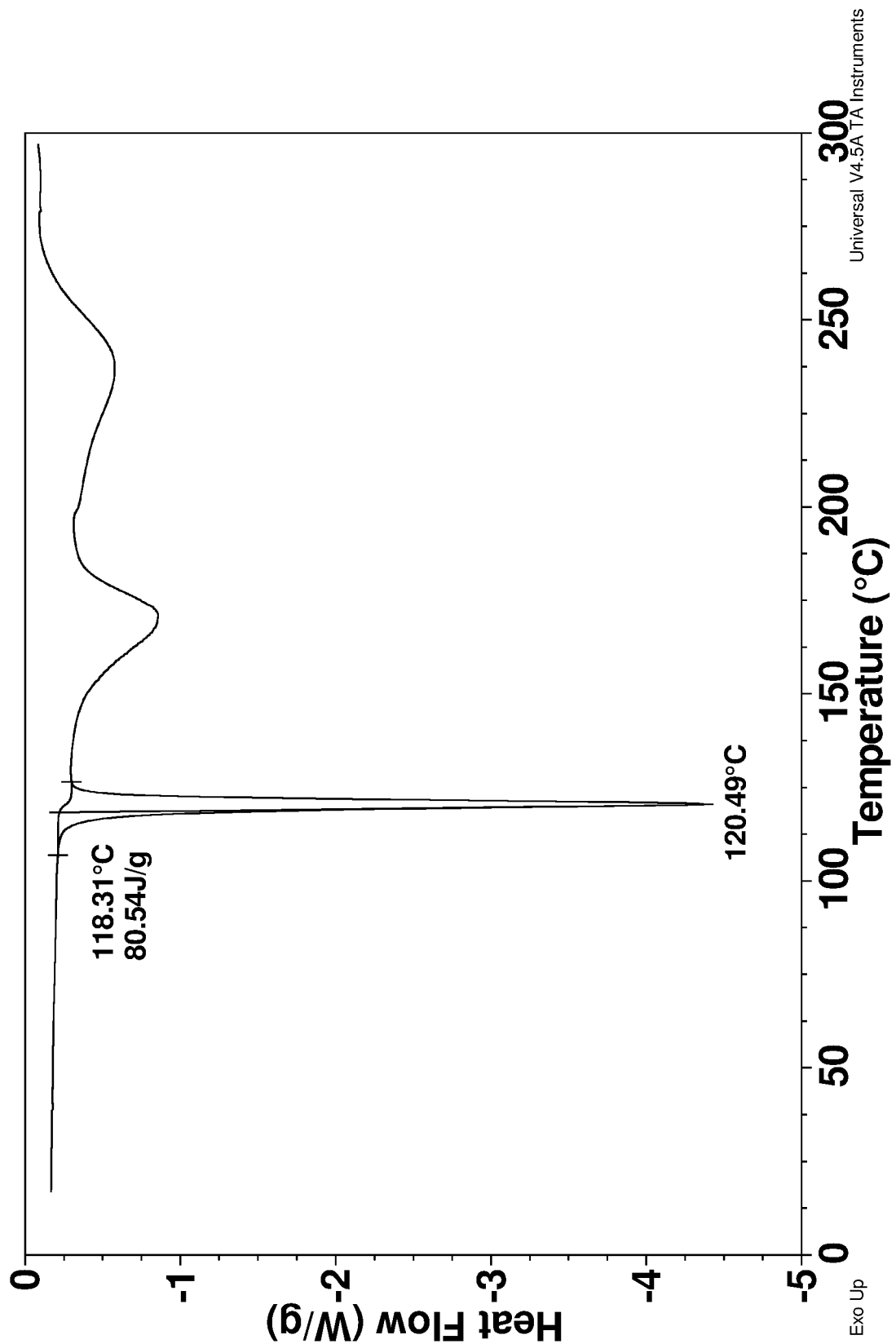
FIG. 18: DSC for Tenofovir Alafenamide Bis-Xinafoate

CRYSTALLINE FORMS OF TENOFOVIR ALAFENAMIDE

CROSS-REFERENCE TO RELATED APPLICATIONS

This application is a continuation of U.S. patent application Ser. No. 16/360,763, filed Mar. 21, 2019, which is a divisional of U.S. patent application Ser. No. 15/882,784, filed Jan. 29, 2018, which claims priority benefit to U.S. Provisional Application Ser. No. 62/452,428, filed on Jan. 31, 2017, the disclosures of which are incorporated by reference in their entirety.

FIELD

The present invention relates to novel crystalline forms of salts and/or co-crystals of tenofovir alafenamide, and the pharmaceutical formulations and therapeutic uses thereof.

BACKGROUND

As discussed in PCT Publication no. WO2002/008241, tenofovir alafenamide demonstrates antiviral activity.

Tenofovir alafenamide has the following structure:

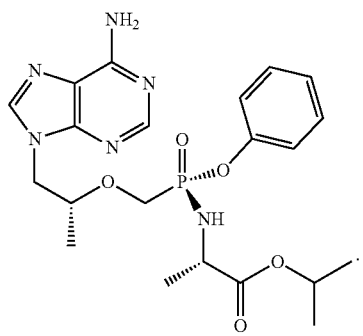 [SMILES: CC(C)OC(=O)[C@H](C)N[P@](=O)(CO[C@H](C)Cn1cnc2c(N)ncnc21)Oc1ccccc1]

Stable forms of the tenofovir alafenamide with suitable chemical and physical stability are desired.

SUMMARY

In some embodiments, the present invention is directed to novel crystalline forms of salts and/or co-crystals of tenofovir alafenamide.

In some embodiments, the present invention is directed to solid Tenofovir Alafenamide Hemipamoate. In some embodiments, the present invention is directed to crystalline Tenofovir Alafenamide Hemipamoate Form I. In some embodiments, the present invention is directed to crystalline Tenofovir Alafenamide Hemipamoate Form II.

In some embodiments, the present invention is directed to solid Tenofovir Alafenamide Sebacate. In some embodiments, the present invention is directed to crystalline Tenofovir Alafenamide Sebacate Form I.

In some embodiments, the present invention is directed to solid Tenofovir Alafenamide Napsylate. In some embodiments, the present invention is directed to crystalline Tenofovir Alafenamide Napsylate Form I.

In some embodiments, the present invention is directed to solid Tenofovir Alafenamide Orotate. In some embodiments, the present invention is directed to crystalline Tenofovir Alafenamide Orotate Form I. In some embodiments, the present invention is directed to crystalline Tenofovir Alafenamide Orotate Form II. In some embodiments, the present invention is directed to crystalline Tenofovir Alafenamide Orotate Form III.

In some embodiments, the present invention is directed to solid Tenofovir Alafenamide Vanillate. In some embodiments, the present invention is directed to crystalline Tenofovir Alafenamide Vanillate.

In some embodiments, the present invention is directed to solid Tenofovir Alafenamide Bis-Xinafoate. In some embodiments, the present invention is directed to crystalline Tenofovir Alafenamide Bis-Xinafoate.

In some embodiments, the present invention is directed to methods of treating an HIV infection by administering a therapeutically effective amount of a salt and/or co-crystal of tenofovir alafenamide provided herein.

In some embodiments, the present invention is directed to a salt and/or co-crystal of tenofovir alafenamide provided herein for use in methods of treating an HIV infection.

In some embodiments, the present invention is directed to the use of a salt and/or co-crystal of tenofovir alafenamide provided herein in the manufacture of a medicament for treating an HIV infection.

DESCRIPTION OF THE FIGURES

FIG. 1 shows an XRPD pattern of Tenofovir Alafenamide Hemipamoate Form I.

FIG. 2 shows a DSC thermogram of Tenofovir Alafenamide Hemipamoate Form I.

FIG. 3 shows an XRPD pattern of Tenofovir Alafenamide Hemipamoate Form II.

FIG. 4 shows a DSC thermogram of Tenofovir Alafenamide Hemipamoate Form II.

FIG. 5 shows an XRPD pattern of Tenofovir Alafenamide Sebacate Form I.

FIG. 6 shows a DSC thermogram of Tenofovir Alafenamide Sebacate Form I.

FIG. 7 shows an XRPD pattern of Tenofovir Alafenamide Napsylate Form I.

FIG. 8 shows a DSC thermogram of Tenofovir Alafenamide Napsylate Form I.

FIG. 9 shows an XRPD pattern of Tenofovir Alafenamide Orotate Form I.

FIG. 10 shows a DSC thermogram of Tenofovir Alafenamide Orotate Form I.

FIG. 11 shows an XRPD pattern of Tenofovir Alafenamide Orotate Form II.

FIG. 12 shows a DSC thermogram of Tenofovir Alafenamide Orotate Form II.

FIG. 13 shows an XRPD pattern of Tenofovir Alafenamide Orotate Form III.

FIG. 14 shows a DSC thermogram of Tenofovir Alafenamide Orotate Form III.

FIG. 15 shows an XRPD pattern of Tenofovir Alafenamide Vanillate.

FIG. 16 shows a DSC thermogram of Tenofovir Alafenamide Vanillate.

FIG. 17 shows an XRPD pattern of Tenofovir Alafenamide Bis-Xinafoate.

FIG. 18 shows a DSC thermogram of Tenofovir Alafenamide Bis-Xinafoate.

DETAILED DESCRIPTION

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments that reference throughout this specification to "a compound" includes the solid, crystalline, salt, and co-crystal forms of tenofovir alafenamide disclosed herein.

The appearance or the phrase "a compound" or "a compound described herein" refers to a salt and/or co-crystal of tenofovir alafenamide. Accordingly, "a salt and/or co-crystal of tenofovir alafenamide" comprises Tenofovir Alafenamide Hemipamoate Form I, Tenofovir Alafenamide Hemipamoate Form II, Tenofovir Alafenamide Sebacate Form I, Tenofovir Alafenamide Napsylate Form I, Tenofovir Alafenamide Orotate Form I, Tenofovir Alafenamide Orotate Form II, and Tenofovir Alafenamide Form III.

In addition, "a salt and/or co-crystal of Tenofovir Alafenamide" comprises Tenofovir Alafenamide Vanillate and Tenofovir Alafenamide Bis-Xinafoate.

The invention disclosed herein is also meant to encompass all pharmaceutically acceptable salts and/or co-crystals of tenofovir alafenamide being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled salts and/or co-crystals of tenofovir alafenamide, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled salts and/or co-crystals of tenofovir alafenamide can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, and/or emulsifier, or a combination of one or more of the above which has been approved by the United States Food and Drug Administration as being acceptable for use in humans or domestic animals.

A "pharmaceutical composition" refers to a formulation of a compound of the invention (e.g., a salt and/or co-crystal of tenofovir alafenamide) and a medium generally accepted in the art for the delivery of the biologically active compound to mammals, e.g., humans. Such a medium includes all pharmaceutically acceptable excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above. In certain embodiments, the term "treatment" is intended to mean the administration of a compound or composition according to the present invention to alleviate or eliminate symptoms of an HIV infection and/or to reduce viral load in a patient. In certain embodiments, the term "treatment" as used herein is intended to mean the administration of a compound or composition according to the present invention to alleviate or eliminate symptoms of an HIV infection and/or to reduce viral load in a patient. In certain embodiments, the term "treatment" as used herein is further or alternatively intended to mean the administration of a compound or composition according to the present invention to maintain a reduced viral load in a patient. In certain embodiments, the term "treatment" as used herein is further or alternatively intended to mean the administration of a compound or composition according to the present invention post-exposure of the individual to the virus as a subsequent or additional therapy to a first-line therapy (e.g., for maintenance of low viral load).

"Prevention" or "preventing" means any treatment of a disease or condition that causes the clinical symptoms of the disease or condition not to develop. The term "prevention" also encompasses the administration of a therapeutically effective amount of a compound or composition according to the present invention pre-exposure of the individual to the virus (e.g., pre-exposure prophylaxis), to prevent the appearance of symptoms of the disease and/or to prevent the virus from reaching detectible levels in the blood.

The terms "subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In some embodiments, the subject (or the patient) is a human. "Human (or patient) in need thereof" refers to a human who may have or is suspect to have diseases or conditions that would benefit from certain treatment; for example, being treated with the compounds disclosed herein according to the present application.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical excipient.

The term "substantially as shown in" when referring, for example, to an XRPD pattern, or a DSC thermogram, refers to a thermogram or graph that is not necessarily identical to those depicted herein, but that falls within the limits of experimental error or deviations when considered by one of ordinary skill in the art.

In some embodiments, the term "substantially pure" or "substantially free" with respect to a particular crystalline form of a compound means that the composition comprising the crystalline form contains less than 99%, less than 95%, less than 90%, less than 85%, less than 80%, less than 75%, less than 70%, less than 65%, less than 60%, less than 55%, less than 50%, less than 40%, less than 30%, less than 20%, less than 15%, less than 10%, less than 5%, or less than 1% by weight of other substances, including other crystalline forms and/or impurities. In certain embodiments, "substantially pure" or "substantially free of" refers to a substance free of other substances, including other crystalline forms and/or impurities. Impurities may, for example, include by-products or left over reagents from chemical reactions, contaminants, degradation products, other crystalline forms, water, and solvents.

Crystalline Forms of Salts and/or Co-Crystals of Tenofovir Alafenamide

It is desirable to develop a crystalline form of a salt and/or co-crystal of tenofovir alafenamide that may be useful in the synthesis of a salt and/or co-crystal of tenofovir alafenamide. A crystalline form of a salt and/or co-crystal of tenofovir alafenamide may be an intermediate to the synthesis of a salt and/or co-crystal of tenofovir alafenamide. A crystalline form may have properties such as bioavailability, stability, purity, and/or manufacturability at certain conditions that may be suitable for medical or pharmaceutical uses.

Crystalline forms of salts and/or co-crystals of tenofovir alafenamide, including substantially pure forms, may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of salts and/or co-crystals of tenofovir alafenamide may provide advantages such as improving: the manufacturing process of the compound, the stability or storability of a drug product form of the compound, the stability or storability of a drug substance of the compound and/or the bioavailability and/or stability of the compound as an active agent.

The use of certain solvents and/or processes have been found to produce different crystalline forms of the salts and/or co-crystals of tenofovir alafenamide described herein which may exhibit one or more favorable characteristics described above. The processes for the preparation of the crystalline forms described herein and characterization of these crystalline forms are described in detail below.

One skilled in the art understands that a compound structure may be named or identified using commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure for tenofovir alafenamide provided above may also be named or identified as (S)-isopropyl 2-(((S)-((((R)-1-(6-amino-9H-purin-9-yl)propan-2-yl)oxy) methyl)(phenoxy)phosphoryl)amino)propanoate under IUPAC and CAS Registry Number 379270-37-8.

In some embodiments, solid salts and/or co-crystals of tenofovir alafenamide are disclosed. In some embodiments, crystalline forms of salts and/or co-crystals of tenofovir alafenamide are disclosed.

Tenofovir Alafenamide Hemipamoate

In some embodiments, provided is solid Tenofovir Alafenamide Hemipamoate. In some embodiments, provided is a crystalline form of Tenofovir Alafenamide Hemipamoate. In some embodiments, provided is crystalline Tenofovir Alafenamide Hemipamoate Form I. In some embodiments, provided is crystalline Tenofovir Alafenamide Hemipamoate Form II.

Tenofovir Alafenamide Hemipamoate Form I

In some embodiments, provided is crystalline Tenofovir Alafenamide Hemipamoate Form I, wherein the crystal structure exhibits an X-ray powder diffraction (XRPD) pattern substantially as shown in FIG. 1. Crystalline Tenofovir Alafenamide Hemipamoate Form I may exhibit a differential scanning calorimetry (DSC) thermogram substantially as shown in FIG. 2.

In some embodiments crystalline Tenofovir Alafenamide Hemipamoate Form I, at least one, or both (a)-(b) apply: (a) crystalline Tenofovir Alafenamide Hemipamoate Form I has an XRPD pattern substantially as shown in FIG. 1; (b) crystalline Tenofovir Alafenamide Hemipamoate Form I has a DSC thermogram substantially as shown in FIG. 2.

In some embodiments, crystalline Tenofovir Alafenamide Hemipamoate Form I has the following properties:
  an XRPD pattern substantially as shown in FIG. 1
  a DSC themogram substantially as shown in FIG. 2

In some embodiments, crystalline Tenofovir Alafenamide Hemipamoate Form I has an XRPD pattern displaying at least two, at least three, at least four, at least five, at least six, at least seven, or at least eight of the degree 2θ-reflections with the greatest intensity as the XRPD pattern substantially as shown in FIG. 1.

In certain embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, and 22.3°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, and 22.3° and one or more of the degree 2θ-reflections (+/− 0.2 degrees 2θ) at 19.0°, 25.7°, 20.1°, 23.8° and 17.4°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, and 22.3° and one of the degree 2θ-reflections (+/− 0.2 degrees 2θ) at 19.0°, 25.7°, 20.1°, 23.8° and 17.4°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, and 22.3° and two of the degree 2θ-reflections (+/− 0.2 degrees 2θ) at 19.0°, 25.7°, 20.1°, 23.8° and 17.4°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, and 22.3° and three of the degree 2θ-reflections (+/− 0.2 degrees 2θ) at 19.0°, 25.7°, 20.1°, 23.8° and 17.4°. In some embodiments, crystalline Tenofovir Alafenamide Hemipamoate Form I has an XRPD pattern comprising degree 2-reflections (+/− 0.2 degrees 2θ) at 7.4°, 8.4°, 10.6°, 14.8°, and 22.3° and four of the degree 2θ-reflections (+/− 0.2 degrees 2θ) at 19.0°, 25.7°, 20.1°, 23.8° and 17.4°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4°.

In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 11.2°, 13.1°, 13.8°, 14.8°, 15.8°, 17.4°, 19.0°, 20.1°, 21.0°, 22.3°, 23.8°, 25.7°, and 28.8°.

In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and one or more of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and one of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and two of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and three of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and four of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and five of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and six of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 14.8°, 22.3°, 19.0°, 25.7°, 20.1°, 23.8° and 17.4° and seven of the degree 2θ-reflections (+/− 0.2 degrees 2θ) at 21.0°, 15.8°, 11.2°, 28.8°, 13.1°, 30.6°, 32.9°, and 13.8°. In some embodiments, crystalline Tenofovir Alafenamide Hemipamoate Form I has an XRPD pattern comprising degree 2θ-reflections (+/− 0.2 degrees 2θ) at 7.4°, 8.4°, 10.6°, 11.2°, 13.1°, 13.8°, 14.8°, 15.8°, 17.4°, 19.0°, 20.1°, 21.0°, 22.3°, 23.8°, 25.7°, 28.8°, 30.6°, and 32.9°. In some embodiments, crystalline Tenofovir Alafenamide Hemipamoate Form I has an XRPD pattern comprising any five degree 2θ-reflections (+/− 0.2 degrees 2θ) selected from the group consisting of 7.4°, 8.4°, 10.6°, 11.2°, 13.1°, 13.8°, 14.8°, 15.8°, 17.4°, 19.0°, 20.1°, 21.0°, 22.3°, 23.8°, 25.7°, 28.8°, 30.6°, and 32.9°. In some embodiments, crystalline Tenofovir Alafenamide Hemipamoate Form I has an XRPD pattern comprising any seven degree 2θ-reflections (+/− 0.2 degrees 2θ) selected from the group consisting of 7.4°, 8.4°, 10.6°, 11.2°, 13.1°, 13.8°, 14.8°, 15.8°, 17.4°, 19.0°, 20.1°, 21.0°, 22.3°, 23.8°, 25.7°, 28.8°, 30.6°, and 32.9°. In some embodiments, crystalline Tenofovir Alafenamide Hemipamoate Form I has an XRPD pattern comprising any ten degree 2θ-reflections (+/− 0.2 degrees 2θ) selected from the group consisting of 7.4°, 8.4°, 10.6°, 11.2°, 13.1°, 13.8°, 14.8°, 15.8°, 17.4°, 19.0°, 20.1°, 21.0°, 22.3°, 23.8°, 25.7°, 28.8°, 30.6°, and 32.9°.

Tenofovir Alafenamide Hemipamoate Form II

In some embodiments, provided is crystalline Tenofovir Alafenamide Hemipamoate Form II, wherein the crystal structure exhibits an X-ray powder diffraction (XRPD) pattern substantially as shown in FIG. 3. Crystalline Tenofovir Alafenamide Hemipamoate Form II may exhibit a differential scanning calorimetry (DSC) thermogram substantially as shown in FIG. 4.

In some embodiments crystalline Tenofovir Alafenamide Hemipamoate Form II, at least one, or both (a)-(b) apply: (a) crystalline Tenofovir Alafenamide Hemipamoate Form II has an XRPD pattern substantially as shown in FIG. 3; (b) crystalline Tenofovir Alafenamide Hemipamoate Form II has a DSC thermogram substantially as shown in FIG. 4.

In some embodiments, crystalline Tenofovir Alafenamide Hemipamoate Form II has the following properties:
an XRPD pattern substantially as shown in FIG. 3
a DSC thermogram substantially as shown in FIG. 4

In some embodiments, crystalline Tenofovir Alafenamide Hemipamoate Form II has an XRPD pattern displaying at least two, at least three, at least four, at least five, at least six, at least seven, or at least eight of the degree 2θ-reflections with the greatest intensity as the XRPD pattern substantially as shown in FIG. 3.

In certain embodiments, crystalline Tenofovir Alafenamide Hemipamoate Form II has an XRPD pattern comprising degree 2θ-reflections (+/− 0.2 degrees 2θ) at 5.5°, 10.9°, 16.2°, 22.1°, and 23.2°. In some embodiments, crystalline Tenofovir Alafenamide Hemipamoate Form II has an XRPD pattern comprising degree 2θ-reflections (+/− 0.2 degrees 2θ) at 5.5°, 10.9°, 16.2°, 22.1°, and 23.2° and one or more of the degree 2θ-reflections (+/− 0.2 degrees 2θ) at 24.1°, 27.6°, and 29.0°. In some embodiments, crystalline Tenofovir Alafenamide Hemipamoate Form II has an XRPD pattern comprising degree 2θ-reflections (+/− 0.2 degrees 2θ) at 5.5°, 10.9°, 16.2°, 22.1°, and 23.2° and one of the degree 2θ-reflections (+/− 0.2 degrees 2θ) at 24.1°, 27.6°, and 29.0°. In some embodiments, crystalline Tenofovir Alafenamide Hemipamoate Form II has an XRPD pattern comprising degree 2θ-reflections (+/− 0.2 degrees 2θ) at 5.5°, 10.9°, 16.2°, 22.1°, and 23.2° and two of the degree 2θ-reflections (+/− 0.2 degrees 2θ) at 24.1°, 27.6°, and 29.0°. In some embodiments, crystalline Tenofovir Alafenamide Hemipamoate Form II has an XRPD pattern comprising degree 2θ-reflections (+/− 0.2 degrees 2θ) at 5.5°, 10.9°, 16.2°, 22.1°, 23.2°, and 24.1°. In some embodiments, crystalline Tenofovir Alafenamide Hemipamoate Form II has an XRPD pattern comprising degree 2θ-reflections (+/− 0.2 degrees 2θ) at 5.5°, 10.9°, 16.2°, 22.1°, 23.2°, 24.1°, 27.6°, and 29.0°.

In some embodiments, crystalline Tenofovir Alafenamide Hemipamoate Form II has an XRPD pattern comprising any five degree 2θ-reflections (+/− 0.2 degrees 2θ) selected from the group consisting of 5.5°, 10.9°, 16.2°, 22.1°, 23.2°, 24.1°, 27.6°, and 29.0°. In some embodiments, crystalline Tenofovir Alafenamide Hemipamoate Form I has an XRPD pattern comprising any seven degree 2θ-reflections (+/− 0.2 degrees 2θ) selected from the group consisting of 5.5°, 10.9°, 16.2°, 22.1°, 23.2°, 24.1°, 27.6°, and 29.0°.

Tenofovir Alafenamide Sebacate

In some embodiments, provided is solid Tenofovir Alafenamide Sebacate. In some embodiments, provided is a crystalline form of Tenofovir Alafenamide Sebacate. In some embodiments, provided is crystalline Tenofovir Alafenamide Sebacate Form I.

Tenofovir Alafenamide Sebacate Form I

In some embodiments, provided is crystalline Tenofovir Alafenamide Sebacate Form I, wherein the crystal structure exhibits an X-ray powder diffraction (XRPD) pattern substantially as shown in FIG. 5. Crystalline Tenofovir Alafenamide Sebacate Form I may exhibit a differential scanning calorimetry (DSC) thermogram substantially as shown in FIG. 6.

In some embodiments crystalline Tenofovir Alafenamide Sebacate Form I, at least one, at least two, or all of the following (a)-(b) apply: (a) crystalline Tenofovir Alafenamide Sebacate Form I has an XRPD pattern substantially as shown in FIG. 5; (b) crystalline Tenofovir Alafenamide Sebacate Form I has a DSC thermogram substantially as shown in FIG. 6.

In some embodiments, crystalline Tenofovir Alafenamide Sebacate Form I has the following properties:
an XRPD pattern substantially as shown in FIG. 5
a DSC thermogram substantially as shown in FIG. 6

In some embodiments, crystalline Tenofovir Alafenamide Sebacate Form I has an XRPD pattern displaying at least two, at least three, at least four, at least five, at least six, at least seven, or at least eight of the degree 2θ-reflections with the greatest intensity as the XRPD pattern substantially as shown in FIG. 5.

In certain embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, and 19.8°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, and 19.8° and one or more of the degree 2θ-reflections (+/− 0.2 degrees 2θ) at 14.8°, 15.7°, 18.7°, 19.3° and 22.1°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, and 19.8° and one of the degree 2θ-reflections (+/− 0.2 degrees 2θ) at 14.8°, 15.7°, 18.7°, 19.3° and 22.1°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, and 19.8° and two of the degree 2θ-reflections (+/− 0.2 degrees 2θ) at 14.8°, 15.7°, 18.7°, 19.3° and 22.1°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, and 19.8° and three of the degree 2θ-reflections (+/− 0.2 degrees 2θ) at 14.8°, 15.7°, 18.7°, 19.3° and 22.1°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, and 19.8° and four of the degree 2θ-reflections (+/− 0.2 degrees 2θ) at 14.8°, 15.7°, 18.7°, 19.3° and 22.1°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1°.

In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and one or more of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and one of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and two of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and three of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and four of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and five of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and six of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 14.8°, 15.7°, 18.7°, 19.3°, 19.8°, and 22.1° and seven of the degree 2θ-reflections (+/− 0.2 degrees 2θ) at 11.7°, 12.6°, 20.9°, 23.4°, 23.8°, 26.2°, 28.2°, and 29.0°. In some embodiments, crystalline Tenofovir Alafenamide Sebacate Form I has an XRPD pattern comprising degree 2θ-reflections (+/− 0.2 degrees 2θ) at 5.3°, 6.6°, 9.4°, 9.6°, 11.7°, 12.6°, 14.8°, 15.7°, 18.7°, 19.3°, 19.8°, 20.9°, 22.1°, 23.4°, 23.8°, 26.2°, 28.2°, and 29.0°. In some embodiments, crystalline Tenofovir Alafenamide Sebacate Form I has an XRPD pattern comprising any five degree 2θ-reflections (+/− 0.2 degrees 2θ) selected from the group consisting of 5.3°, 6.6°, 9.4°, 9.6°, 10.5°, 11.7°, 12.6°, 14.0°, 14.8°, 15.7°, 16.9°, 18.7°, 19.3°, 19.8°, 20.9°, 21.6°, 22.1°, 22.9°, 23.4°, 23.8°, 25.3°, 26.2°, 26.5°, 27.4°, 28.2°, 28.7°, 29.0°, 33.3°, and 37.9°. In some embodiments, crystalline Tenofovir Alafenamide Sebacate Form I has an XRPD pattern comprising any seven degree 2θ-reflections (+/− 0.2 degrees 2θ) selected from the group consisting of 5.3°, 6.6°, 9.4°, 9.6°, 10.5°, 11.7°, 12.6°, 14.0°, 14.8°, 15.7°, 16.9°, 18.7°, 19.3°, 19.8°, 20.9°, 21.6°, 22.1°, 22.9°, 23.4°, 23.8°, 25.3°, 26.2°, 26.5°, 27.4°, 28.2°, 28.7°, 29.0°, 33.3°, and 37.9°. In some embodiments, crystalline Tenofovir Alafenamide Sebacate Form I has an XRPD pattern comprising any ten degree 2θ-reflections (+/− 0.2 degrees 2θ) selected from the group consisting of 5.3°, 6.6°, 9.4°, 9.6°, 10.5°, 11.7°, 12.6°, 14.0°, 14.8°, 15.7°, 16.9°, 18.7°, 19.3°, 19.8°, 20.9°, 21.6°, 22.1°, 22.9°, 23.4°, 23.8°, 25.3°, 26.2°, 26.5°, 27.4°, 28.2°, 28.7°, 29.0°, 33.3°, and 37.9°.

Tenofovir Alafenamide Napsylate

In some embodiments, provided is solid Tenofovir Alafenamide Napsylate. In some embodiments, provided is a crystalline form of Tenofovir Alafenamide Napsylate. In some embodiments, provided is crystalline Tenofovir Alafenamide Napsylate Form I.

Tenofovir Alafenamide Napsylate Form I

In some embodiments, provided is crystalline Tenofovir Alafenamide Napsylate Form I, wherein the crystal structure exhibits an X-ray powder diffraction (XRPD) pattern substantially as shown in FIG. 7. Crystalline Tenofovir Alafenamide Napsylate Form I may exhibit a differential scanning calorimetry (DSC) thermogram substantially as shown in FIG. 8.

In some embodiments crystalline Tenofovir Alafenamide Napsylate Form I, at least one, or all of the following (a)-(b) apply: (a) crystalline Tenofovir Alafenamide Napsylate Form I has an XRPD pattern substantially as shown in FIG. 7; (b) crystalline Tenofovir Alafenamide Napsylate Form I has a DSC thermogram substantially as shown in FIG. 8.

In some embodiments, crystalline Tenofovir Alafenamide Napsylate Form I has the following properties:
an XRPD pattern substantially as shown in FIG. 7
a DSC thermogram substantially as shown in FIG. 8

In some embodiments, crystalline Tenofovir Alafenamide Napsylate Form I has an XRPD pattern displaying at least two, at least three, at least four, at least five, at least six, at least seven, or at least eight of the degree 2θ-reflections with the greatest intensity as the XRPD pattern substantially as shown in FIG. 7.

In certain embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, and 19.2°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, and 19.2° and one or more of the degree 2θ-reflections (+/− 0.2 degrees 2θ) at 19.4°, 19.8°, 20.6°, 23.8° and 27.2°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, and 19.2° and one of the degree 2θ-reflections (+/− 0.2 degrees 2θ) at 19.4°, 19.8°, 20.6°, 23.8° and 27.2°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, and 19.2° and two of the degree 2θ-reflections (+/− 0.2 degrees 2θ) at 19.4°, 19.8°, 20.6°, 23.8° and 27.2°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, and 19.2° and three of the degree 2θ-reflections (+/− 0.2 degrees 2θ) at 19.4°, 19.8°, 20.6°, 23.8° and 27.2°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, and 19.2° and four of the degree 2θ-reflections (+/− 0.2 degrees 2θ) at 19.4°, 19.8°, 20.6°, 23.8° and 27.2°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2°.

In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and one or more of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and one of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and two of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and three of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and four of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and five of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and six of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 13.6°, 15.3°, 19.2°, 19.4°, 19.8°, 20.6°, 23.8° and 27.2° and seven of the degree 2θ-reflections (+/− 0.2 degrees 2θ) at 9.8°, 13.2°, 15.5°, 16.5°, 17.8°, 23.0°, 24.1°, and 26.0°. In some embodiments, crystalline Tenofovir Alafenamide Napsylate Form I has an XRPD pattern comprising degree 2θ-reflections (+/− 0.2 degrees 2θ) at 3.9°, 7.8°, 9.8°, 13.2°, 13.6°, 15.3°, 15.5°, 16.5°, 17.8°, 19.2°, 19.4°, 19.8°, 20.6°, 23.0°, 23.8°, 24.1°, 26.0°, and 27.2°. In some embodiments, crystalline Tenofovir Alafenamide Napsylate Form I has an XRPD pattern comprising any five degree 2θ-reflections (+/− 0.2 degrees 2θ) selected from the group consisting of 3.9°, 7.8°, 9.8°, 10.3°, 11.6°, 13.2°, 13.6°, 15.3°, 15.5°, 16.5°, 17.8°, 18.2°, 19.2°, 19.4°, 19.8°, 20.1°, 20.6°, 23.0°, 23.3°, 23.8°, 24.1°, 24.5°, 26.0°, 27.2°, 28.3°, 29.5°, 32.2°, 34.3°, 35.2°, 36.9°, 38.2°, and 39.2°. In some embodiments, crystalline Tenofovir Alafenamide Napsylate Form I has an XRPD pattern comprising any seven degree 2θ-reflections (+/− 0.2 degrees 2θ) selected from the group consisting of 3.9°, 7.8°, 9.8°, 10.3°, 11.6°, 13.2°, 13.6°, 15.3°, 15.5°, 16.5°, 17.8°, 18.2°, 19.2°, 19.4°, 19.8°, 20.1°, 20.6°, 23.0°, 23.3°, 23.8°, 24.1°, 24.5°, 26.0°, 27.2°, 28.3°, 29.5°, 32.2°, 34.3°, 35.2°, 36.9°, 38.2°, and 39.2°. In some embodiments, crystalline Tenofovir Alafenamide Napsylate Form I has an XRPD pattern comprising any ten degree 2θ-reflections (+/− 0.2 degrees 2θ) selected from the group consisting of 3.9°, 7.8°, 9.8°, 10.3°, 11.6°, 13.2°, 13.6°, 15.3°, 15.5°, 16.5°, 17.8°, 18.2°, 19.2°, 19.4°, 19.8°, 20.1°, 20.6°, 23.0°, 23.3°, 23.8°, 24.1°, 24.5°, 26.0°, 27.2°, 28.3°, 29.5°, 32.2°, 34.3°, 35.2°, 36.9°, 38.2°, and 39.2°.

Tenofovir Alafenamide Orotate

In some embodiments, provided is solid Tenofovir Alafenamide Orotate. In some embodiments, provided is a crystalline form of Tenofovir Alafenamide Orotate. In some embodiments, provided is crystalline Tenofovir Alafenamide Orotate Form I. In some embodiments, provided is crystalline Tenofovir Alafenamide Orotate Form II. In some embodiments, provided is crystalline Tenofovir Alafenamide Orotate Form III.

Tenofovir Alafenamide Orotate Form I

In some embodiments, provided is crystalline Tenofovir Alafenamide Orotate Form I, wherein the crystal structure exhibits an X-ray powder diffraction (XRPD) pattern substantially as shown in FIG. 9. Crystalline Tenofovir Alafenamide Orotate Form I may exhibit a differential scanning calorimetry (DSC) thermogram substantially as shown in FIG. 10.

In some embodiments crystalline Tenofovir Alafenamide Orotate Form I, at least one, or all of the following (a)-(b) apply: (a) crystalline Tenofovir Alafenamide Orotate Form I has an XRPD pattern substantially as shown in FIG. 9; (b) crystalline Tenofovir Alafenamide Orotate Form I has a DSC thermogram substantially as shown in FIG. 10.

In some embodiments, crystalline Tenofovir Alafenamide Orotate Form I has the following properties:
an XRPD pattern substantially as shown in FIG. 9
a DSC themogram substantially as shown in FIG. 10

In some embodiments, crystalline Tenofovir Alafenamide Orotate Form I has an XRPD pattern displaying at least two, at least three, at least four, at least five, at least six, at least seven, or at least eight of the degree 2θ-reflections with the greatest intensity as the XRPD pattern substantially as shown in FIG. 9.

In certain embodiments, crystalline Tenofovir Alafenamide Orotate Form I has an XRPD pattern comprising degree 2θ-reflections (+/− 0.2 degrees 2θ) at 3.0°, 5.9°, 8.9°, and 11.8°. In some embodiments, crystalline Tenofovir Alafenamide Orotate Form I has an XRPD pattern comprising degree 2θ-reflections (+/− 0.2 degrees 2θ) at 3.0°, 5.9°, 8.9°, and 11.8° and one or more of the degree 2θ-reflections (+/− 0.2 degrees 2θ) at 14.8°, 16.0°, 17.7°, 18.7° and 21.5°. In some embodiments, crystalline Tenofovir Alafenamide Orotate Form I has an XRPD pattern comprising degree 2θ-reflections (+/− 0.2 degrees 2θ) at 3.0°, 5.9°, 8.9°, and 11.8° and one of the degree 2θ-reflections (+/− 0.2 degrees 2θ) at 14.8°, 16.0°, 17.7°, 18.7° and 21.5°. In some embodiments, crystalline Tenofovir Alafenamide Orotate Form I has an XRPD pattern comprising degree 2θ-reflections (+/− 0.2 degrees 2θ) at 3.0°, 5.9°, 8.9°, and 11.8° and two of the degree 2θ-reflections (+/− 0.2 degrees 2θ) at 14.8°, 16.0°, 17.7°, 18.7° and 21.5°. In some embodiments, crystalline Tenofovir Alafenamide Orotate Form I has an XRPD pattern comprising degree 2θ-reflections (+/− 0.2 degrees 2θ) at 3.0°, 5.9°, 8.9°, and 11.8° and three of the degree 2θ-reflections (+/− 0.2 degrees 2θ) at 14.8°, 16.0°, 17.7°, 18.7° and 21.5°. In some embodiments, crystalline Tenofovir Alafenamide Orotate Form I has an XRPD pattern comprising degree 2θ-reflections (+/− 0.2 degrees 2θ) at 3.0°, 5.9°, 8.9°, and 11.8° and four of the degree 2θ-reflections (+/− 0.2 degrees 2θ) at 14.8°, 16.0°, 17.7°, 18.7° and 21.5°. In some embodiments, crystalline Tenofovir Alafenamide Orotate Form I has an XRPD pattern comprising degree 2θ-reflections (+/− 0.2 degrees 2θ) at 3.0°, 5.9°, 8.9°, 11.8°, 14.8°, 16.0°, 17.7°, 18.7° and 21.5°.

In some embodiments, crystalline Tenofovir Alafenamide Orotate Form I has an XRPD pattern comprising degree 2θ-reflections (+/− 0.2 degrees 2θ) at 3.0°, 3.5°, 5.9°, 8.9°, 11.8°, 14.8°, 16.0°, 17.7°, 18.7° and 21.5° and one or more of the degree 2θ-reflections (+/− 0.2 degrees 2θ) at 27.2°, 28.7°, and 31.5°. In some embodiments, crystalline Tenofovir Alafenamide Orotate Form I has an XRPD pattern comprising degree 2θ-reflections (+/− 0.2 degrees 2θ) at 3.0°, 3.5°, 5.9°, 8.9°, 11.8°, 14.8°, 16.0°, 17.7°, 18.7° and 21.5° and one of the degree 2θ-reflections (+/− 0.2 degrees 2θ) at 27.2°, 28.7°, and 31.5°. In some embodiments, crystalline Tenofovir Alafenamide Orotate Form I has an XRPD pattern comprising degree 2θ-reflections (+/−0.2 degrees 2θ) at 3.0°, 3.5°, 5.9°, 8.9°, of the degree 2θ-reflections (+/− 0.2 degrees 2θ) at 27.2°, 28.7°, and 31.5°. In some embodiments, crystalline Tenofovir Alafenamide Orotate Form I has an XRPD pattern comprising degree 2θ-reflections (+/− 0.2 degrees 2θ) at 3.0°, 3.5°, 5.9°, 8.9°, 11.8°, 14.8°, 16.0°, 17.7°, 18.7°, 21.5°, 27.2°, 28.7°, and 31.5°. In some embodiments, crystalline Tenofovir Alafenamide Orotate Form I has an XRPD pattern comprising any five degree 2θ-reflections (+/− 0.2 degrees 2θ) selected from the group consisting of 3.0°, 3.5°, 5.9°, 8.9°, 11.8°, 14.8°, 16.0°, 17.7°, 18.7°, 21.5°, 27.2°, 28.7°, and 31.5°. In some embodiments, crystalline Tenofovir Alafenamide Orotate Form I has an XRPD pattern comprising any seven degree 2θ-reflections (+/− 0.2 degrees 2θ) selected from the group consisting of 3.0°, 3.5°, 5.9°, 8.9°, 11.8°, 14.8°, 16.0°, 17.7°, 18.7°, 21.5°, 27.2°, 28.7°, and 31.5°. In some embodiments, crystalline Tenofovir Alafenamide Orotate Form I has an XRPD pattern comprising any ten degree 2θ-reflections (+/− 0.2 degrees 2θ) selected from the group consisting of 3.0°, 3.5°, 5.9°, 8.9°, 11.8°, 14.8°, 16.0°, 17.7°, 18.7°, 21.5°, 27.2°, 28.7°, and 31.5°.

Tenofovir Alafenamide Orotate Form II

In some embodiments, provided is crystalline Tenofovir Alafenamide Orotate Form II, wherein the crystal structure exhibits an X-ray powder diffraction (XRPD) pattern substantially as shown in FIG. 11. Crystalline Tenofovir Alafenamide Orotate Form II may exhibit a differential scanning calorimetry (DSC) thermogram substantially as shown in FIG. 12.

In some embodiments crystalline Tenofovir Alafenamide Orotate Form II, at least one, or all of the following (a)-(b) apply: (a) crystalline Tenofovir Alafenamide Orotate Form II has an XRPD pattern substantially as shown in FIG. 11; (b) crystalline Tenofovir Alafenamide Orotate Form II has a DSC thermogram substantially as shown in FIG. 12.

In some embodiments, crystalline Tenofovir Alafenamide Orotate Form II has the following properties:
an XRPD pattern substantially as shown in FIG. 11
a DSC themogram substantially as shown in FIG. 12

In some embodiments, crystalline Tenofovir Alafenamide Orotate Form II has an XRPD pattern displaying at least two, at least three, at least four, at least five, at least six, at least seven, or at least eight of the degree 2θ-reflections with the greatest intensity as the XRPD pattern substantially as shown in FIG. 11.

In certain embodiments, crystalline Tenofovir Alafenamide Orotate Form II has an XRPD pattern comprising degree 2θ-reflections (+/− 0.2 degrees 2θ) at 3.4°, 3.8°, 6.9°, 10.3°, and 13.8°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, and 13.8° and one or more of the degree 2θ-reflections (+/− 0.2 degrees 2θ) at 15.4°, 17.3°, 19.0°, 22.8° and 29.0°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, and 13.8° and one of the degree 2θ-reflections (+/− 0.2 degrees 2θ) at 15.4°, 17.3°, 19.0°, 22.8° and 29.0°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, and 13.8° and two of the degree 2θ-reflections (+/− 0.2 degrees 2θ) at 15.4°, 17.3°, 19.0°, 22.8° and 29.0°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, and 13.8° and three of the degree 2θ-reflections (+/− 0.2 degrees 2θ) at 15.4°, 17.3°, 19.0°, 22.8° and 29.0°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, and 13.8° and four of the degree 2θ-reflections (+/− 0.2 degrees 2θ) at 15.4°, 17.3°, 19.0°, 22.8° and 29.0°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, 13.8°, 15.4°, 17.3°, 19.0°, 22.8° and 29.0°.

In some embodiments, crystalline Tenofovir Alafenamide Orotate Form II has an XRPD pattern comprising degree 2θ-reflections (+/− 0.2 degrees 2θ) at 3.4°, 6.9°, 10.3°, 13.8°, 15.4°, 17.3°, 19.0°, 22.8° and 29.0° and one or more of the degree 2θ-reflections (+/− 0.2 degrees 2θ) at 18.4° and 21.6°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, 13.8°, 15.4°, 17.3°, 19.0°, 22.8° and 29.0° and one of the degree 2θ-reflections (+/− 0.2 degrees 2θ) at 18.4° and 21.6°. In some embodiments, crystalline Tenofovir Alafenamide Orotate Form II has an XRPD pattern comprising degree 2θ-reflections (+/− 0.2 degrees 2θ) at 3.4°, 6.9°, 10.3°, 13.8°, 15.4°, 17.3°, 18.4°, 19.0°, 21.6° 22.8°, and 29.0°. In some embodiments, crystalline Tenofovir Alafenamide Orotate Form II has an XRPD pattern comprising any five degree 2θ-reflections (+/− 0.2 degrees 2θ) selected from the group consisting of 3.4°, 3.8°, 6.9°, 10.3°, 13.8°, 15.4°, 17.3°, 18.4°, 19.0°, 21.6° 22.8°, and 29.0°. In some embodiments, crystalline Tenofovir Alafenamide Orotate Form II has an XRPD pattern comprising any seven degree 2θ-reflections (+/− 0.2 degrees 2θ) selected from the group consisting of 3.4°, 3.8°, 6.9°, 10.3°, 13.8°, 15.4°, 17.3°, 18.4°, 19.0°, 21.6° 22.8°, and 29.0°. In some embodiments, crystalline Tenofovir Alafenamide Orotate Form II has an XRPD pattern comprising any ten degree 2θ-reflections (+/− 0.2 degrees 2θ) selected from the group consisting of 3.4°, 3.8°, 6.9°, 10.3°, 13.8°, 15.4°, 17.3°, 18.4°, 19.0°, 21.6° 22.8°, and 29.0°.

Tenofovir Alafenamide Orotate Form III

In some embodiments, provided is crystalline Tenofovir Alafenamide Orotate Form III, wherein the crystal structure exhibits an X-ray powder diffraction (XRPD) pattern substantially as shown in FIG. 13. Crystalline Tenofovir Alafenamide Orotate Form III may exhibit a differential scanning calorimetry (DSC) thermogram substantially as shown in FIG. 14.

In some embodiments crystalline Tenofovir Alafenamide Orotate Form III, at least one, or all of the following (a)-(b) apply: (a) crystalline Tenofovir Alafenamide Orotate Form III has an XRPD pattern substantially as shown in FIG. 13; (b) crystalline Tenofovir Alafenamide Orotate Form III has a DSC thermogram substantially as shown in FIG. 14.

In some embodiments, crystalline Tenofovir Alafenamide Orotate Form III has the following properties:
an XRPD pattern substantially as shown in FIG. 13
a DSC themogram substantially as shown in FIG. 14

In some embodiments, crystalline Tenofovir Alafenamide Orotate Form III has an XRPD pattern displaying at least two, at least three, at least four, at least five, at least six, at least seven, or at least eight of the degree 2θ-reflections with the greatest intensity as the XRPD pattern substantially as shown in FIG. 13.

In certain embodiments, crystalline Tenofovir Alafenamide Orotate Form III has an XRPD pattern comprising degree 2θ-reflections (+/− 0.2 degrees 2θ) at 3.8°, 9.4°, 12.4°, 15.7°, and 19.0°. In some embodiments, crystalline Tenofovir Alafenamide Orotate Form III has an XRPD pattern comprising degree 2θ-reflections (+/− 0.2 degrees 2θ) at 3.8°, 9.4°, 12.4°, 15.7°, and 19.0° and one or more of the degree 2θ-reflections (+/− 0.2 degrees 2θ) at 8.3°, 16.4°, 24.5°, 26.6° and 28.9°. In some embodiments, crystalline Tenofovir Alafenamide Orotate Form III has an XRPD pattern comprising degree 2θ-reflections (+/− 0.2 degrees 2θ) at 3.8°, 9.4°, 12.4°, 15.7°, and 19.0° and one of the degree 2θ-reflections (+/− 0.2 degrees 2θ) at 8.3°, 16.4°, 24.5°, 26.6° and 28.9°. In some embodiments, crystalline Tenofovir Alafenamide Orotate Form III has an XRPD pattern comprising degree 2θ-reflections (+/− 0.2 degrees 2θ) at 3.8°, 9.4°, 12.4°, 15.7°, and 19.0° and two of the degree 2θ-reflections (+/− 0.2 degrees 2θ) at 8.3°, 16.4°, 24.5°, 26.6° and 28.9°. In some embodiments, crystalline Tenofovir Alafenamide Orotate Form III has an XRPD pattern comprising degree 2θ-reflections (+/− 0.2 degrees 2θ) at 3.8°, 9.4°, 12.4°, 15.7°, and 19.0° and three of the degree 2θ-reflections (+/− 0.2 degrees 2θ) at 8.3°, 16.4°, 24.5°, 26.6° and 28.9°. In some embodiments, crystalline Tenofovir Alafenamide Orotate Form III has an XRPD pattern comprising degree 2θ-reflections (+/− 0.2 degrees 2θ) at 3.8°, 9.4°, 12.4°, 15.7°, and 19.0° and four of the degree 2θ-reflections (+/− 0.2 degrees 2θ) at 8.3°, 16.4°, 24.5°, 26.6° and 28.9°. In some embodiments, crystalline Tenofovir Alafenamide Orotate Form III has an XRPD pattern comprising degree 2θ-reflections (+/− 0.2 degrees 2θ) at 3.8°, 8.3°, 9.4°, 12.4°, 15.7°, 16.4°, 19.0°, 24.5°, 26.6° and 28.9°.

In some embodiments, crystalline Tenofovir Alafenamide Orotate Form III has an XRPD pattern comprising degree 2θ-reflections (+/− 0.2 degrees 2θ) at 3.8°, 8.3°, 9.4°, 12.4°, 15.7°, 16.4°, 19.0°, 24.5°, 26.6° and 28.9° and one or more of the degree 2θ-reflections (+/− 0.2 degrees 2θ) at 6.9°, 22.8°, and 27.6°. In some embodiments, crystalline Tenofovir Alafenamide Orotate Form III has an XRPD pattern comprising degree 2θ-reflections (+/− 0.2 degrees 2θ) at 3.8°, 8.3°, 9.4°, 12.4°, 15.7°, 16.4°, 19.0°, 24.5°, 26.6° and 28.9° and one of the degree 2θ-reflections (+/− 0.2 degrees 2θ) at 6.9°, 22.8°, and 27.6°. In some embodiments, crystalline Tenofovir Alafenamide Orotate Form III has an XRPD pattern comprising degree 2θ-reflections (+/− 0.2 degrees 2θ) at 3.8°, 8.3°, 9.4°, 12.4°, 15.7°, 16.4°, 19.0°, 24.5°, 26.6° and 28.9° and two of the degree 2θ-reflections (+/− 0.2 degrees 2θ) at 6.9°, 22.8°, and 27.6°. In some embodiments, crystalline Tenofovir Alafenamide Orotate Form III has an XRPD pattern comprising degree 2θ-reflections (+/− 0.2 degrees 2θ) at 3.8°, 6.9°, 8.3°, 9.4°, 12.4°, 15.7°, 16.4°, 19.0°, 22.8°, 24.5°, 26.6°, 27.6°, and 28.9°. In some embodiments, crystalline Tenofovir Alafenamide Orotate Form III has an XRPD pattern comprising any five degree 2θ-reflections (+/− 0.2 degrees 2θ) selected from the group consisting of 3.8°, 6.9°, 8.3°, 9.4°, 12.4°, 15.7°, 16.4°, 19.0°, 22.8°, 24.5°, 26.6°, 27.6°, and 28.9°. In some embodiments, crystalline Tenofovir Alafenamide Orotate Form III has an XRPD pattern comprising any seven degree 2θ-reflections (+/− 0.2 degrees 2θ) selected from the group consisting of 3.8°, 6.9°, 8.3°, 9.4°, 12.4°, 15.7°, 16.4°, 19.0°, 22.8°, 24.5°, 26.6°, 27.6°, and 28.9°. In some embodiments, crystalline Tenofovir Alafenamide Orotate Form III has an XRPD pattern comprising any ten degree 2θ-reflections (+/− 0.2 degrees 2θ) selected from the group consisting of 3.8°, 6.9°, 8.3°, 9.4°, 12.4°, 15.7°, 16.4°, 19.0°, 22.8°, 24.5°, 26.6°, 27.6°, and 28.9°.

Tenofovir Alafenamide Vanillate

In some embodiments, provided is solid Tenofovir Alafenamide Vanillate. In some embodiments, provided is a crystalline form of Tenofovir Alafenamide Vanillate.

Tenofovir Alafenamide Vanillate

In some embodiments, provided is crystalline Tenofovir Alafenamide Vanillate, wherein the crystal structure exhibits an XRPD pattern substantially as shown in FIG. 15. Crystalline Tenofovir Alafenamide Vanillate may exhibit a DSC thermogram substantially as shown in FIG. 16.

In some embodiments crystalline Tenofovir Alafenamide Vanillate, at least one, at least two, or all of the following (a)-(b) apply: (a) crystalline Tenofovir Alafenamide Vanillate has an XRPD pattern substantially as shown in FIG. 15; (b) crystalline Tenofovir Alafenamide Vanillate has a DSC thermogram substantially as shown in FIG. 16.

In some embodiments, crystalline Tenofovir Alafenamide Vanillate has the following properties:
an XRPD pattern substantially as shown in FIG. 15
a DSC themogram substantially as shown in FIG. 16.

In some embodiments, crystalline Tenofovir Alafenamide Vanillate has an XRPD pattern displaying at least two, at least three, at least four, at least five, at least six, at least seven, or at least eight of the degree 2θ-reflections with the greatest intensity as the XRPD pattern substantially as shown in FIG. 15.

In certain embodiments, crystalline Tenofovir Alafenamide Vanillate has an XRPD pattern comprising degree 2θ-reflections (+/− 0.2 degrees 2θ) at 6.6°, 9.3°, and 22.8°. In some embodiments, crystalline Tenofovir Alafenamide Vanillate has an XRPD pattern comprising degree 2θ-reflections (+/− 0.2 degrees 2θ) at 6.6°, 9.3°, and 22.8° and one or more of the degree 2θ-reflections (+/− 0.2 degrees 2θ) at 14.2°, 15.2°, 19.0°, and 19.8°. In some embodiments, crystalline Tenofovir Alafenamide Vanillate has an XRPD pattern comprising degree 2θ-reflections (+/− 0.2 degrees 2θ) at 6.6°, 9.3°, and 22.8° and one of the degree 2θ-reflections (+/− 0.2 degrees 2θ) at 14.2°, 15.2°, 19.0°, and 19.8°. In some embodiments, crystalline Tenofovir Alafenamide Vanillate has an XRPD pattern comprising degree 2θ-reflections (+/− 0.2 degrees 2θ) at 6.6°, 9.3°, and 22.8° and two of the degree 2θ-reflections (+/− 0.2 degrees 2θ) at 14.2°, 15.2°, 19.0°, and 19.8°. In some embodiments, crystalline Tenofovir Alafenamide Vanillate has an XRPD pattern comprising degree 2θ-reflections (+/− 0.2 degrees 2θ) at 6.6°, 9.3°, and 22.8° and three of the degree 2θ-reflections (+/− 0.2 degrees 2θ) at 14.2°, 15.2°, 19.0°, and 19.8°. In some embodiments, crystalline Tenofovir Alafenamide Vanillate has an XRPD pattern comprising degree 2θ-reflections (+/− 0.2 degrees 2θ) at 6.6°, 9.3°, and 22.8° and four of the degree 2θ-reflections (+/− 0.2 degrees 2θ) at 14.2°, 15.2°, 19.0°, and 19.8°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, 19.8°, and 22.8°.

In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and one or more of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and one of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and two of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and three of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and four of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and five of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and six of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 14.2°, 15.2°, 19.0°, and 22.8° and seven of the degree 2θ-reflections (+/− 0.2 degrees 2θ) at 10.8°, 12.3°, 18.4°, 19.8°, 22.1°, 25.0°, and 32.4°. In some embodiments, crystalline Tenofovir Alafenamide Vanillate has an XRPD pattern comprising degree 2θ-reflections (+/− 0.2 degrees 2θ) at 6.6°, 9.3°, 10.8°, 12.3°, 14.2°, 15.2°, 18.4°, 19.0°, 19.8°, 22.1°, 22.8°, 25.0°, and 32.4°. In some embodiments, crystalline Tenofovir Alafenamide Vanillate has an XRPD pattern comprising any five degree 2θ-reflections (+/− 0.2 degrees 2θ) selected from the group consisting of 6.6°, 9.3°, 10.8°, 12.3°, 14.2°, 15.2°, 15.9°, 18.4°, 19.0°, 19.8°, 21.6°, 22.1°, 22.8°, 25.0°, 27.7°, and 32.4°. In some embodiments, crystalline Tenofovir Alafenamide Vanillate has an XRPD pattern comprising any seven degree 2θ-reflections (+/− 0.2 degrees 2θ) selected from the group consisting of 6.6°, 9.3°, 10.8°, 12.3°, 14.2°, 15.2°, 15.9°, 18.4°, 19.0°, 19.8°, 21.6°, 22.1°, 22.8°, 25.0°, 27.7°, and 32.4°.. In some embodiments, crystalline Tenofovir Alafenamide Vanillate has an XRPD pattern comprising any ten degree 2θ-reflections (+/− 0.2 degrees 2θ) selected from the group consisting of 6.6°, 9.3°, 10.8°, 12.3°, 14.2°, 15.2°, 15.9°, 18.4°, 19.0°, 19.8°, 21.6°, 22.1°, 22.8°, 25.0°, 27.7°, and 32.4°.

Tenofovir Alafenamide Bis-Xinafoate

In some embodiments, provided is solid Tenofovir Alafenamide Bis-Xinafoate. In some embodiments, provided is a crystalline form of Tenofovir Alafenamide Bis-Xinafoate.

Tenofovir Alafenamide Bis-Xinafoate

In some embodiments, provided is crystalline Tenofovir Alafenamide Bis-Xinafoate, wherein the crystal structure exhibits an XRPD pattern substantially as shown in FIG. 17. Crystalline Tenofovir Alafenamide Bis-Xinafoate may exhibit a DSC thermogram substantially as shown in FIG. 18.

In some embodiments crystalline Tenofovir Alafenamide Bis-Xinafoate, at least one, at least two, or all of the following (a)-(b) apply: (a) crystalline Tenofovir Alafenamide Bis-Xinafoate has an XRPD pattern substantially as shown in FIG. 17; (b) crystalline Tenofovir Alafenamide Bis-Xinafoate has a DSC thermogram substantially as shown in FIG. 18.

In some embodiments, crystalline Tenofovir Alafenamide Bis-Xinafoate has the following properties:
an XRPD pattern substantially as shown in FIG. 17
a DSC themogram substantially as shown in FIG. 18.

In some embodiments, crystalline Tenofovir Alafenamide Bis-Xinafoate has an XRPD pattern displaying at least two, at least three, at least four, at least five, at least six, at least seven, or at least eight of the degree 2θ-reflections with the greatest intensity as the XRPD pattern substantially as shown in FIG. 17.

In certain embodiments, crystalline Tenofovir Alafenamide Bis-Xinafoate has an XRPD pattern comprising degree 2θ-reflections (+/− 0.2 degrees 2θ) at 4.5°, 8.9°, 14.4°, and 15.4°. In some embodiments, crystalline Tenofovir Alafenamide Bis-Xinafoate has an XRPD pattern comprising degree 2θ-reflections (+/− 0.2 degrees 2θ) at 4.5°, 8.9°, 14.4°, and 15.4° and one or more of the degree 2θ-reflections (+/− 0.2 degrees 2θ) at 7.7°, 11.2°, 18.8°, 21.7°, and 25.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 14.4°, and 15.4° and one of the degree 2θ-reflections (+/− 0.2 degrees 2θ) at 7.7°, 11.2°, 18.8°, 21.7°, and 25.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 14.4°, and 15.4° and two of the degree 2θ-reflections (+/− 0.2 degrees 2θ) at 7.7°, 11.2°, 18.8°, 21.7°, and 25.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 14.4°, and 15.4° and three of the degree 2θ-reflections (+/− 0.2 degrees 2θ) at 7.7°, 11.2°, 18.8°, 21.7°, and 25.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 14.4°, and 15.4° and four of the degree 2θ-reflections (+/− 0.2 degrees 2θ) at 7.7°, 11.2°, 18.8°, 21.7°, and 25.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5°.

In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and one or more of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and one of the degree 2θ-reflections (+/− 0.2 degrees 2θ) at 7.7°, 18.8°, 21.7°, 21.9°, 25.5°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 44.5°, 8.9°, 11.2°, 14.4°, 15.4°, 18.8°, 21.7°, and 25.5° and two of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and three of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and four of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and five of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and six of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 8.9°, 11.2°, 14.4°, 15.4°, 18.8°, 21.7°, and 25.5° and seven of the degree 2θ-reflections (+/− 0.2 degrees 2θ) at 7.7°, 14.7°, 21.9°, 25.9°, 32.9°, 33.8°, and 36.5°. In some embodiments, crystalline Tenofovir Alafenamide Bis-Xinafoate has an XRPD pattern comprising degree 2θ-reflections (+/− 0.2 degrees 2θ) at 4.5°, 7.7°, 8.9°, 11.2°, 13.4°, 14.4°, 14.7°, 15.4°, 15.7°, 17.0°, 18.3°, 18.8°, 21.7°, 21.9°, 25.5°, 25.9°, 32.9°, 33.8°, and 36.5°. In some embodiments, crystalline Tenofovir Alafenamide Bis-Xinafoate has an XRPD pattern comprising any five degree 2θ-reflections (+/− 0.2 degrees 2θ) selected from the group consisting of 4.5°, 7.7°, 8.9°, 11.2°, 13.4°, 14.4°, 14.7°, 15.4°, 15.7°, 17.0°, 18.3°, 18.8°, 21.7°, 21.9°, 25.5°, 25.9°, 32.9°, 33.8°, and 36.5°. In some embodiments, crystalline Tenofovir Alafenamide Bis-Xinafoate has an XRPD pattern comprising any seven degree 2θ-reflections (+/− 0.2 degrees 2θ) selected from the group consisting of 4.5°, 7.7°, 8.9°, 11.2°, 13.4°, 14.4°, 14.7°, 15.4°, 15.7°, 17.0°, 18.3°, 18.8°, 21.7°, 21.9°, 25.5°, 25.9°, 32.9°, 33.8°, and 36.5°. In some embodiments, crystalline Tenofovir Alafenamide Bis-Xinafoate has an XRPD pattern comprising any ten degree 2θ-reflections (+/− 0.2 degrees 2θ) selected from the group consisting of 4.5°, 7.7°, 8.9°, 11.2°, 13.4°, 14.4°, 14.7°, 15.4°, 15.7°, 17.0°, 18.3°, 18.8°, 21.7°, 21.9°, 25.5°, 25.9°, 32.9°, 33.8°, and 36.5°.

Pharmaceutical Compositions

For the purposes of administration, in certain embodiments, the compounds described herein are administered as a raw chemical or are formulated as pharmaceutical compositions. Pharmaceutical compositions of the present invention comprise a therapeutically effective amount of a salt and/or co-crystal of tenofovir alafenamide provided herein, and a pharmaceutically acceptable excipient. The salt and/or co-crystal of tenofovir alafenamide is present in the composition in an amount which is effective to treat a particular disease or condition of interest. The activity salts and/or co-crystals of tenofovir alafenamide can be determined by one skilled in the art, for example, as described herein. Appropriate therapeutically effective concentrations and dosages can be readily determined by one skilled in the art. In certain embodiments, a salt and/or co-crystal of tenofovir alafenamide is present in the pharmaceutical composition in an amount from about 5 mg to about 1,000 mg. In certain embodiments, a salt and/or co-crystal of tenofovir alafenamide is present in the pharmaceutical composition in an amount from about 5 mg to about 100 mg. In certain embodiments, a salt and/or co-crystal of tenofovir alafenamide is present in the pharmaceutical composition in an amount from about 20 mg to about 75 mg. In certain embodiments, a salt and/or co-crystal of tenofovir alafenamide is present in the pharmaceutical composition in an amount from about 25 mg to about 50 mg. In certain embodiments, a salt and/or co-crystal of tenofovir alafenamide is present in the pharmaceutical composition in an amount of about 25 mg. In certain embodiments, a salt and/or co-crystal of tenofovir alafenamide is present in the pharmaceutical composition in an amount of about 50 mg. In certain embodiments, a salt and/or co-crystal of tenofovir alafenamide is present in the pharmaceutical composition in an amount of about 75 mg. In certain embodiments, a salt and/or co-crystal of tenofovir alafenamide is present in the pharmaceutical composition in an amount of about 100 mg. In certain embodiments, a salt and/or co-crystal of tenofovir alafenamide is present in the pharmaceutical composition in an amount of about 25 mg, 28 mg, 30 mg, 33 mg, 35 mg, 38 mg, 40 mg, 43 mg, 45 mg, 48 mg, or about 50 mg.

In some embodiments, the pharmaceutical composition of the invention administered can be a long-acting formulation.

In some embodiments, the pharmaceutical composition of the invention administered to a subject is active for at least 10 days. In some embodiments, the pharmaceutical composition of the invention administered to a subject is active for at least 15 days. In some embodiments, the pharmaceutical composition of the invention administered to a subject is active for at least 30 days. In some embodiments, the pharmaceutical composition of the invention administered to a subject is active for at least 60 days. In some embodiments, the pharmaceutical composition of the invention administered to a subject is active for at least 90 days. In some embodiments, the pharmaceutical composition of the invention administered to a subject is active for up to 6 months.

Administration of the compounds of the invention in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. The pharmaceutical compositions of the invention can be prepared by combining a compound of the invention with an appropriate pharmaceutically acceptable excipient, and may be formulated into preparations in solid, semi-solid, liquid or gaseous forms, such as solid dispersions and solid solutions. Typical routes of administering such pharmaceutical compositions include, without limitation, oral, topical, transdermal, inhalation, parenteral (including subcutaneous, intramuscular, intravenous, intradermal, intrathecal and epidural), sublingual, buccal, rectal, vaginal, intranasal, and pulmonary. In a specific embodiment, the pharmaceutical composition is a subcutaneous injection. In a specific embodiment, the pharmaceutical composition is in a unit dose form wherein the unit does form is a subcutaneous injection. In a specific embodiment, the pharmaceutical composition is a tablet. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention for treatment of a disease or condition of interest in accordance with the teachings of this invention.

In some embodiments, the pharmaceutical composition of the invention can be administered through intramuscular injection. In particular, reference to "active" includes maintaining a concentration minimum (Cmin) above the efficatious level for HIV.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant or other solubilizing excipient may be added to facilitate the formation of a homogeneous solution or suspension. Surfactants are compounds that non-covalently interact with the compound of the invention so as to facilitate dissolution or homogeneous suspension of the compound in the aqueous delivery system.

In other embodiments, a solid pharmaceutical composition intended for oral administration can be prepared by mixing a therapeutically effective amount of a compound of the invention with at least one suitable pharmaceutically acceptable excipient to form a solid preformulation composition, which then may be readily subdivided into equally effective unit dosage forms such as tablets, pills and capsules. Accordingly, in some embodiments, a pharmaceutical composition is provided, which includes a therapeutically effective amount of a compound of a salt and/or co-crystal of tenofovir alafenamide and a pharmaceutically acceptable excipient.

The compounds of the invention are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some embodiments, the compounds of the invention can be administered alone or in combination with other antiviral agents one time a day, or two times a day, or three times a day, or four times a day, for as long as the patient is infected, latently infected, or to prevent infection (e.g. for multiple years, months, weeks, or days). In some embodiments, the compounds of the invention can be administered alone or in combination with other antiviral agents one time every seven days. In some embodiments, the compounds of the invention can be administered alone or in combination with other antiviral agents one time every fourteen days. In some embodiments, the compounds of the invention can be administered alone or in combination with other antiviral agents one time every twenty-one days. In some embodiments, the compounds of the invention can be administered alone or in combination with other antiviral agents one time every twenty-eight days. In some embodiments, the compounds of the invention can be administered alone or in combination with other antiviral agents one time every month.

Provided are also compositions comprising a salt and/or co-crystal of tenofovir alafenamide as described herein. In a particular embodiment, a composition comprising one of the salts and/or co-crystals of tenofovir alafenamide described herein is provided. In a particular embodiment, a composition comprising two of the salts and/or co-crystals of tenofovir alafenamide described herein is provided. In a particular embodiment, a composition comprising three of the salts and/or co-crystals of tenofovir alafenamide described herein is provided. In a particular embodiment, a composition comprising four of the salts and/or co-crystals of tenofovir alafenamide described herein is provided. In other embodiments, the compositions described herein may comprise substantially pure crystalline forms, or may be substantially free of other crystalline forms and/or impurities.

In some embodiments, the composition comprises a crystalline form of a salt and/or co-crystal of tenofovir alafenamide. In certain embodiments are provided compositions comprising a crystalline form as described herein, wherein the salt and/or co-crystal of tenofovir alafenamide within the composition is substantially pure (i.e., substantially pure Tenofovir Alafenamide Hemipamoate Form I, Tenofovir Alafenamide Hemipamoate Form II, Tenofovir Alafenamide Sebacate Form I, Tenofovir Alafenamide Napsylate Form I, Tenofovir Alafenamide Orotate Form I, Tenofovir Alafenamide Orotate Form II, and Tenofovir Alafenamide Form III described herein). In particular embodiments of compositions comprising a crystalline form of a salt and/or co-crystal of tenofovir alafenamide, at least about 50%, at least about 60%, at least about 70%, at least about 80%, at least about 85%, at least about 90%, at least about 95%, at least about 96%, at least about 97%, at least about 98%, or at least about 99% of the salt and/or co-crystal of tenofovir alafenamide present in the composition is one of the crystalline forms disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the crystalline forms of the salt and/or co-crystal of tenofovir alafenamide.

In certain embodiments are provided compositions comprising a crystalline form as described herein, wherein the salt and/or co-crystal of tenofovir alafenamide within the composition is substantially pure Tenofovir Alafenamide Vanillate and/or Tenofovir Alafenamide Bis-Xinafoate as described herein. In particular embodiments of compositions comprising a crystalline form of a salt and/or co-crystal of tenofovir alafenamide, at least about 50%, at least about 60%, at least about 70%, at least about 80%, at least about 85%, at least about 90%, at least about 95%, at least about 96%, at least about 97%, at least about 98%, or at least about 99% of the salt and/or co-crystal of tenofovir alafenamide present in the composition is Tenofovir Alafenamide Vanillate or Tenofovir Alafenamide Bis-Xinofoate as disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Tenofovir Alafenamide Vanillate or Tenofovir Alafenamide Bis-Xinofoate as disclosed herein.

In other embodiments of compositions comprising a crystalline form disclosed herein, less than about 50%, less than about 40%, less than about 30%, less than about 20%, less than about 10%, less than about 5%, less than about 4%, less than about 3%, less than about 2% or less than about 1% of a salt and/or co-crystal of tenofovir alafenamide present in the composition are other amorphous or crystal forms of the salt and/or co-crystal of tenofovir alafenamide and/or impurities.

In yet other embodiments of compositions comprising the crystalline forms disclosed herein, impurities make up less than about 5%, less than about 4%, less than about 3%, less than about 2% or less than about 1% of the total mass relative to the mass of the crystalline forms present. Impurities may, for example, include by-products from synthesizing a salt and/or co-crystal of tenofovir alafenamide, contaminants, degradation products, other crystalline forms, amorphous form, water, and solvents. In certain embodiments, impurities include by-products from the process of synthesizing a salt and/or co-crystal of tenofovir alafenamide. In certain embodiments, impurities include contaminants from the process of synthesizing a salt and/or co-crystal of tenofovir alafenamide. In certain embodiments, impurities include degradation products of a salt and/or co-crystal of tenofovir alafenamide. In certain embodiments, impurities include other crystalline forms of a salt and/or co-crystal of tenofovir alafenamide. In certain embodiments, impurities include other crystalline forms of a salt and/or co-crystal of tenofovir alafenamide and/or amorphous forms of a salt and/or co-crystal of tenofovir alafenamide. In certain embodiments, impurities include water or solvent. In certain embodiments of compositions comprising a crystalline form disclosed herein, impurities are selected from the group consisting of by-products from synthesizing a salt and/or co-crystal of tenofovir alafenamide, contaminants, degradation products, other crystalline forms, amorphous forms, water, solvents and combinations thereof.

Combination Therapies

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient.

When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptor) 3B3-PE38, BanLec, bentonite-based nanomedicine, fostemsavir trometamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

alpha-4/beta-7 antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti- ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, C4E10, C2F5+ C2G12+C4E10, 3-BNC-117, PGT145, PGT121, MDX010 (ipilimumab), VRC01, A32, 7B2, 10E8, VRC-07-523, VRC-HIVMAB080-00-AB, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/ AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+ FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+ 3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., a salt and/or co-crystal of tenofovir alafenamide) may be combined with one or more additional therapeutic agents in any dosage amount of the compound described herein (e.g., from 1 mg to 500 mg of a salt and/or co-crystal of tenofovir alafenamide).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 1 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Birth control (contraceptive) combination therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In one embodiment, kits comprising a compound disclosed herein, or a pharmaceutically acceptable salt thereof, in combination with one or more (e.g., one, two, three, one or two, or one to three) additional therapeutic agents are provided.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT101.

CAR-T cell therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+T cell, a CD8+T cell, or a combination thereof.

Examples of HIV CAR-T include VC-CAR-T.

TCR-T cell therapy

TCR-T cells are engineered to target HIV derived peptides present on the surface of virus-infected cells.

HBV Combination

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound described herein is formulated as a tablet, which may optionally contain one or more other compounds useful for treating HBV. In certain embodiments, the tablet can contain another active ingredient for treating HBV.

In certain embodiments, such tablets are suitable for once daily dosing.

HBV Combination Therapy

In the above embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylaseinhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A 1 gene inhibitor, SMAC mimetics, Src tyrosine kinase inhibitor, stimulator of interferon gene (STING) agonists, stimulators of NODI, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In certain embodiments, a compound described herein is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein Al modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

In certain embodiments, a compound of the present disclosure, or a pharmaceutically acceptable salt thereof, is combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA)and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, CCC-0975, elvucitabine, ezetimibe, cyclosporin A, gentiopicrin (gentiopicroside), JNJ-56136379, nitazoxanide, birinapant, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD4OL-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, and IR-103.

Toll-like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIB OXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-lb, interferon alpha 1b (HAPGEN®), Veldona, Infradure, Roferon-A, YPEG-interferon alfa-2a (YPEG-rhlFNalpha-2a), P-1101, Algeron, Alfarona, Ingaron (interferon gamma), rSIFN-co (recombinant super compound interferon), Ypeginterferon alfa-2b (YPEG-rhlFNalpha-2b), MOR-22, peginterferon alfa-2b (PEG-INTRON®), Bioferon, Novaferon, Inmutag (Inferon), MULTIFERON®, interferon alfa-nl(HUMOFERON®), interferon beta-la (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-lymphocyte-associated protein 4 (ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in US8513184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404.

Short Interfering RNAs (siRNA)and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X receptor agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein modulators

Nucleoprotein modulators may be either HBV core or capsid protein inhibitors. Examples of nucleoprotein modulators include AT-130, GLS4, NVR-1221, NVR-3778, BAY 41-4109, morphothiadine mesilate, JNJ-379, and DVR-23. Capsid assembly inhibitors such as AB-423.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301,TAK-117, HMPL-689, tenalisib, voxtalisib, and CLR-1401.

Indoleamine-2, 3-dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085(Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in US9186337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase inhibitors

Examples of Arginase inhibitors include CB-1158, C-201, and resminostat.

HBV Combination Therapy

In a particular embodiment, a compound disclosed herein, or a pharmaceutically acceptable salt thereof, is combined with one, two, three, or four additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®)), telbivudine (TYZEKA®), or lamivudine (EPIVIR-HBV®). In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARA- CLUDE®), telbivudine (TYZEKA®), or lamivudine (EPI-VIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPI-VIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A(ᴾ), pegylated interferon alpha-2a (PEGASYS®), interferon alfa-nl(HUMOFERON®), ribavirin, interferon beta-la (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (Bio-Generic Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPI-VIR-HBV), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or a pharmaceutically acceptable salt thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPI-VIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPI-VIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTS®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir)(HEPSERA®, tenofovir disoproxil fumarate)(VIREAD®), tenofovir alafenamide, tenofovir, tenofovir disoproxil, tenofovir alafenamide fumarate, tenofovir alafenamide hemifumarate, entecavir)(BARACLUDE®, telbivudine)(TYZEKA®), or lamivudine)(EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir)(HEPSERA®), tenofovir disoproxil fumarate)(VIREAD®), tenofovir alafenamide, tenofovir, tenofovir disoproxil, tenofovir alafenamide fumarate, tenofovir alafenamide hemifumarate, entecavir)(BARACLUDE®), telbivudine)(TYZEKA®), or lamivudine)(EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Patent No. 8722054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Patent No. 8513184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics),U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085(Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel), US9186337B2 (Oryzon Genomics), and other drugs for treating HBV, and combinations thereof.

In certain embodiments, a compound as disclosed herein (e.g., any salt and/or co-crystal of tenofovir alafenamide) may be combined with one or more (e.g., one, two, three, four, one or two, one to three, or one to four) additional therapeutic agents in any dosage amount of the compounds disclosed herein (e.g., from 10 mg to 1000 mg of any salt and/or co-crystal of tenofovir alafenamide).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a salt and/or co-crystal of tenofovir alafenamide) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a salt and/or co-crystal of tenofovir alafenamide) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

XRPD Data

In certain embodiments, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The characteristic peaks of a given XRPD can be selected according to the peak locations and their relative intensity to conveniently distinguish this crystalline structure from others.

XRPD patterns were collected on a PANanalytical XPERT-PRO diffractometer at ambient conditions under the following experimental settings: 45 KV, 40 mA, Kal=1.5406 Å, scan range 2 to 40°, step size 0.0084 or 0.0167°, measurement time: 5 min.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7-0.3, i.e., about 8.4. Depending on the sample preparation techniques, the calibration techniques applied to the instruments, human operational variation, and etc., those skilled in the art recognize that the appropriate error of margins for a XRPD can be ±0.5; ±0.4; ±0.3; ±0.2; ±0.1; ±0.05; or less. In certain embodiments of the invention, the XRPD margin of error is ±0.05. In certain embodiments of the invention, the XRPD margin of error is ±0.1. In certain embodiments of the invention, the XRPD margin of error is ±0.2. In certain embodiments of the invention, the XRPD margin of error is ±0.5.

Additional details of the methods and equipment used for the XRPD analysis are described in the Examples section.

The XRPD peaks for crystalline Tenofovir Alafenamide Hemipamoate Form I are below in Table 1A.

TABLE 1A

XRPD peaks for crystalline Tenofovir
Alafenamide Hemipamoate Form I
Tenofovir Alafenamide
Hemipamoate Form I

| Peak Position [°2θ] | Relative Intensity [%] |
|---|---|
| 7.4 | 17 |
| 8.4 | 22 |
| 10.6 | 32 |
| 11.2 | 19 |
| 13.1 | 11 |
| 13.8 | 9 |
| 14.8 | 96 |
| 15.8 | 21 |
| 17.4 | 35 |
| 19.0 | 41 |
| 20.1 | 38 |
| 21.0 | 24 |
| 22.3 | 100 |
| 23.8 | 37 |
| 25.7 | 39 |
| 28.8 | 12 |
| 30.6 | 10 |
| 32.9 | 9 |

The XRPD peaks for crystalline Tenofovir Alafenamide Hemipamoate Form II are below in Table 1B.

TABLE 1B

XRPD peaks for crystalline Tenofovir
Alafenamide Hemipamoate Form II
Tenofovir Alafenamide
Hemipamoate Form II

| Peak Position [°2θ] | Relative Intensity [%] |
|---|---|
| 5.5 | 100 |
| 10.9 | 5 |
| 16.2 | 5 |
| 22.1 | 14 |
| 23.2 | 7 |
| 24.1 | 3 |
| 27.6 | 2 |
| 29.0 | 4 |

The XRPD peaks for crystalline Tenofovir Alafenamide Sebacate Form I are below in Table 1C.

TABLE 1C

XRPD peaks for crystalline Tenofovir
Alafenamide Sebacate Form I
Tenofovir Alafenamide
Sebacate Form I

| Peak Position [°2θ] | Relative Intensity [%] |
|---|---|
| 5.3 | 14 |
| 6.6 | 100 |

TABLE 1C-continued

XRPD peaks for crystalline Tenofovir
Alafenamide Sebacate Form I
Tenofovir Alafenamide
Sebacate Form I

| Peak Position [°2θ] | Relative Intensity [%] |
|---|---|
| 9.4 | 70 |
| 9.6 | 76 |
| 10.5 | 5 |
| 11.7 | 29 |
| 12.6 | 10 |
| 14.0 | 6 |
| 14.8 | 41 |
| 15.7 | 38 |
| 16.9 | 9 |
| 18.7 | 51 |
| 19.3 | 44 |
| 19.8 | 57 |
| 20.9 | 11 |
| 21.6 | 7 |
| 22.1 | 38 |
| 22.9 | 7 |
| 23.4 | 22 |
| 23.8 | 22 |
| 25.3 | 7 |
| 26.2 | 18 |
| 26.5 | 9 |
| 27.4 | 7 |
| 28.2 | 12 |
| 28.7 | 5 |
| 29.0 | 11 |
| 33.3 | 6 |
| 37.9 | 6 |

The XRPD peaks for crystalline Tenofovir Alafenamide Napsylate Form I are below in Table 1D.

TABLE 1D

XRPD peaks for crystalline Tenofovir
Alafenamide Napsylate Form I
Tenofovir Alafenamide
Napsylate Form I

| Peak Position [°2θ] | Relative Intensity [%] |
|---|---|
| 3.9 | 50 |
| 7.8 | 94 |
| 9.8 | 26 |
| 10.3 | 13 |
| 11.6 | 9 |
| 13.2 | 25 |
| 13.6 | 49 |
| 15.3 | 52 |
| 15.5 | 32 |
| 16.5 | 21 |
| 17.8 | 24 |
| 18.2 | 6 |
| 19.2 | 100 |
| 19.4 | 60 |
| 19.8 | 65 |
| 20.1 | 19 |
| 20.6 | 43 |
| 23.0 | 36 |
| 23.3 | 19 |
| 23.8 | 49 |
| 24.1 | 42 |
| 24.5 | 19 |
| 26.0 | 36 |
| 27.2 | 99 |
| 28.3 | 16 |
| 29.5 | 6 |
| 32.2 | 20 |

TABLE 1D-continued

XRPD peaks for crystalline Tenofovir
Alafenamide Napsylate Form I
Tenofovir Alafenamide
Napsylate Form I

| Peak Position [°2θ] | Relative Intensity [%] |
|---|---|
| 34.3 | 5 |
| 35.2 | 16 |
| 36.9 | 9 |
| 38.2 | 6 |
| 39.2 | 13 |

The XRPD peaks for crystalline Tenofovir Alafenamide Orotate Form I are below in Table 1E.

TABLE 1E

XRPD peaks for crystalline Tenofovir
Alafenamide Orotate Form I
Tenofovir Alafenamide
Orotate Form I

| Peak Position [°2θ] | Relative Intensity [%] |
|---|---|
| 3.0 | 100 |
| 3.5 | 21 |
| 5.9 | 6 |
| 8.9 | 21 |
| 11.8 | 7 |
| 14.8 | 2 |
| 16.0 | 3 |
| 17.7 | 3 |
| 18.7 | 4 |
| 21.5 | 3 |
| 27.2 | 2 |
| 28.7 | 2 |
| 31.5 | 2 |

The XRPD peaks for crystalline Tenofovir Alafenamide Orotate Form II are below in Table 1F.

TABLE 1F

XRPD peaks for crystalline Tenofovir
Alafenamide Orotate Form II
Tenofovir Alafenamide
Orotate Form II

| Peak Position [°2θ] | Relative Intensity [%] |
|---|---|
| 3.4 | 100 |
| 3.8 | 31 |
| 6.9 | 13 |
| 10.3 | 28 |
| 13.8 | 42 |
| 15.4 | 16 |
| 17.3 | 10 |
| 18.4 | 7 |
| 19.0 | 8 |
| 21.6 | 4 |
| 22.8 | 9 |
| 29.0 | 7 |

The XRPD peaks for crystalline Tenofovir Alafenamide Orotate Form III are below in Table 1G.

TABLE 1G

XRPD peaks for crystalline Tenofovir Alafenamide Orotate Form III
Tenofovir Alafenamide Orotate Form III

| Peak Position [°2θ] | Relative Intensity [%] |
| --- | --- |
| 3.8 | 100 |
| 6.9 | 9 |
| 8.3 | 12 |
| 9.4 | 14 |
| 12.4 | 20 |
| 15.7 | 28 |
| 16.4 | 14 |
| 19.0 | 27 |
| 22.8 | 7 |
| 24.5 | 11 |
| 26.6 | 11 |
| 27.6 | 5 |
| 28.9 | 14 |

The XRPD peaks for crystalline Tenofovir Alafenamide Vanillate are below in Table 1H.

TABLE 1H

XRPD peaks for crystalline Tenofovir Alafenamide Vanillate
Tenofovir Alafenamide Vanillate

| Peak Position [°2θ] | Relative Intensity [%] |
| --- | --- |
| 6.6 | 53 |
| 8.1 | 10 |
| 9.3 | 37 |
| 10.8 | 20 |
| 12.3 | 19 |
| 13.0 | 14 |
| 14.2 | 29 |
| 15.2 | 99 |
| 15.9 | 28 |
| 18.4 | 50 |
| 19.0 | 75 |
| 19.8 | 49 |
| 21.6 | 24 |
| 22.1 | 47 |
| 22.8 | 100 |
| 25.0 | 30 |
| 26.2 | 14 |
| 27.1 | 16 |
| 27.7 | 18 |
| 29.1 | 7 |
| 30.2 | 8 |
| 31.6 | 6 |
| 32.4 | 38 |
| 34.7 | 2 |
| 36.6 | 8 |
| 37.2 | 10 |
| 39.1 | 7 |

The XRPD peaks for crystalline Tenofovir Alafenamide Bis-Xinafoate are below in Table 1I.

TABLE 1I

XRPD peaks for crystalline Tenofovir Alafenamide Bis-Xinafoate
Tenofovir Alafenamide Bis-Xinafoate

| Pos. [°2Th.] | Rel. Int. [%] |
| --- | --- |
| 4.5 | 8 |
| 6.4 | 3 |
| 7.7 | 5 |
| 8.9 | 12 |
| 11.2 | 18 |
| 12.7 | 4 |
| 13.4 | 7 |
| 14.4 | 100 |
| 14.7 | 23 |
| 15.4 | 72 |
| 15.7 | 8 |
| 17.0 | 6 |
| 18.3 | 9 |
| 18.8 | 21 |
| 21.7 | 32 |
| 21.9 | 16 |
| 23.3 | 3 |
| 24.1 | 4 |
| 25.5 | 17 |
| 25.9 | 14 |
| 27.5 | 4 |
| 29.5 | 4 |
| 32.9 | 11 |
| 33.8 | 5 |
| 36.5 | 7 |
| 38.1 | 4 |

Preparation of Crystalline Forms

One method of synthesizing tenofovir alafenamide has been previously described in PCT Publication no. WO2002/008241, filed Jul. 20, 2001. This reference is hereby incorporated herein by reference in its entirety, and specifically with respect to the synthesis of tenofovir alafenamide.

For example, in one aspect, provided is a method of producing a composition comprising one or more crystalline forms of a salt and/or co-crystal of tenofovir alafenamide, wherein the method comprises combining a salt and/or co-crystal of tenofovir alafenamide with a suitable solvent or a mixture of suitable solvents to produce a composition comprising one or more crystalline forms of a salt and/or co-crystal of tenofovir alafenamide. In another aspect, provided is another method of producing a composition comprising one or more crystalline forms of a salt and/or co-crystal of tenofovir alafenamide, wherein the method comprises combining a salt and/or co-crystal of tenofovir alafenamide with a suitable solvent or a mixture of suitable solvents.

The choice of a particular solvent or combination of solvents or method of combining solvents affects the formation favoring one crystalline form of tenofovir alafenamide over another. Solvents suitable for crystal formation may include, for example: tetrahydrofuran, acetone, ethanol, acetonitrile, isopropyl alcohol, methyl ethyl ketone, dichloromethane, 2-methyltetrahydrofuran, ethyl acetate, methyl tert-butyl ether, toluene, water, and any mixture thereof.

The presence of impurities may affect the formation favoring one crystalline form of tenofovir alafenamide over another. In some embodiments, the form is prepared by a process comprising tenofovir alafenamide having impurities. In another embodiment, the form is prepared by a process comprising substantially pure tenofovir alafenamide.

In another aspect, provided is also one or more crystalline forms of tenofovir alafenamide produced according to any of the methods described herein. In another aspect, provided is also one or more crystalline forms of a salt and/or co-crystal of tenofovir alafenamide produced according to any of the methods described herein.

It should be understood that the methods for preparing the crystalline forms described herein may yield quantity and quality differences compared to the methods for preparing tenofovir alafenamide produced on laboratory scale.

Tenofovir Alafenamide Hemipamoate

In some embodiments, provided is a method of preparing Tenofovir Alafenamide Hemipamoate, wherein the method comprises combining tenofovir alafenamide with pamoic acid. In some embodiments, provided is a method of preparing Tenofovir Alafenamide Hemipamoate, wherein the method comprises combining tenofovir alafenamide with pamoic acid and tetrahydrofuran. In some embodiments, provided is a method of preparing Tenofovir Alafenamide Hemipamoate, wherein the method comprises combining tenofovir alafenamide with pamoic acid and tetrahydrofuran at about 50 to 60° C. In some embodiments, provided is a method of preparing Tenofovir Alafenamide Hemipamoate, wherein the method comprises combining tenofovir alafenamide with pamoic acid and tetrahydrofuran at about 50 to 60° C. in an open vial with natural evaporation.

Tenofovir Alafenamide Hemipamoate Form I

In some embodiments, provided is a method of producing a composition comprising crystalline Tenofovir Alafenamide Hemipamoate Form I, wherein the method comprise combining Tenofovir Alafenamide Hemipamoate with a solvent. In some embodiments, the method of producing a composition comprising crystalline Tenofovir Alafenamide Hemipamoate Form I comprises combining Tenofovir Alafenamide Hemipamoate with a solvent selected from water, ethanol, acetonitrile, acetone, isopropyl alcohol, methyl ethyl ketone, dichloromethane, 2-methyltetrahydrofuran, ethyl acetate, methyl tert-butyl ether, and toluene, and any mixture thereof.

Provided is crystalline Tenofovir Alafenamide Hemipamoate Form I produced by combining Tenofovir Alafenamide Hemipamoate and a solvent. Provided is crystalline Tenofovir Alafenamide Hemipamoate Form I produced by combining Tenofovir Alafenamide Hemipamoate and a solvent, wherein the solvent is selected from water, ethanol, acetonitrile, acetone, isopropyl alcohol, methyl ethyl ketone, dichloromethane, 2-methyltetrahydrofuran, ethyl acetate, methyl tert-butyl ether, and toluene, and any mixture thereof.

Tenofovir Alafenamide Hemipamoate Form II

In some embodiments, provided is a method of producing a composition comprising crystalline Tenofovir Alafenamide Hemipamoate Form II, wherein the method comprise combining Tenofovir Alafenamide Hemipamoate with a solvent. In some embodiments, the method of producing a composition comprising crystalline Tenofovir Alafenamide Hemipamoate Form II comprises combining Tenofovir Alafenamide Hemipamoate with dichloromethane.

Provided is crystalline Tenofovir Alafenamide Hemipamoate Form II produced by combining Tenofovir Alafenamide Hemipamoate and a solvent. Provided is crystalline Tenofovir Alafenamide Hemipamoate Form II produced by combining Tenofovir Alafenamide Hemipamoate and dichloromethane.

Tenofovir Alafenamide Sebacate

In some embodiments, provided is a method of preparing Tenofovir Alafenamide Sebacate, wherein the method comprises combining tenofovir alafenamide with sebacic acid. In some embodiments, provided is a method of preparing Tenofovir Alafenamide Sebacate, wherein the method comprises combining tenofovir alafenamide with sebacic acid and acetone. In some embodiments, provided is a method of preparing Tenofovir Alafenamide Sebacate, wherein the method comprises combining tenofovir alafenamide with sebacic acid and acetone in an open vial with natural evaporation.

Tenofovir Alafenamide Sebacate Form I

In some embodiments, provided is a method of producing a composition comprising crystalline Tenofovir Alafenamide Sebacate Form I, wherein the method comprise combining Tenofovir Alafenamide Sebacate with a solvent. In some embodiments, the method of producing a composition comprising crystalline Tenofovir Alafenamide Sebacate Form I comprises combining Tenofovir Alafenamide Sebacate with a solvent selected from tetrahydrofuan and heptane, and any mixture thereof.

Provided is crystalline Tenofovir Alafenamide Sebacate Form I produced by combining Tenofovir Alafenamide Sebacate and a solvent. Provided is crystalline Tenofovir Alafenamide Sebacate Form I produced by combining Tenofovir Alafenamide Sebacate and a solvent selected from tetrahydrofuan and heptane, and any mixture thereof.

Tenofovir Alafenamide Napsylate

In some embodiments, provided is a method of preparing Tenofovir Alafenamide Napsylate, wherein the method comprises combining tenofovir alafenamide with 2-naphthalenesulfonic acid. In some embodiments, provided is a method of preparing Tenofovir Alafenamide Napsylate, wherein the method comprises combining tenofovir alafenamide with 2-naphthalenesulfonic acid and acetone.

Tenofovir Alafenamide Napsylate Form I

In some embodiments, provided is a method of producing a composition comprising crystalline Tenofovir Alafenamide Napsylate Form I, wherein the method comprise combining Tenofovir Alafenamide with 2-naphthalenesulfonic acid and acetone in an open vial with natural evaporation.

Provided is crystalline Tenofovir Alafenamide Napsylate Form I produced by combining Tenofovir Alafenamide with 2-naphthalenesulfonic acid and acetone in an open vial with natural evaporation.

Tenofovir Alafenamide Orotate

In some embodiments, provided is a method of preparing Tenofovir Alafenamide Orotate, wherein the method comprises combining tenofovir alafenamide with orotic acid. In some embodiments, provided is a method of preparing Tenofovir Alafenamide Orotate, wherein the method comprises combining tenofovir alafenamide with orotic acid and acetone.

Tenofovir Alafenamide Orotate Form I

In some embodiments, provided is a method of producing a composition comprising crystalline Tenofovir Alafenamide Orotate Form I, wherein the method comprise combining Tenofovir Alafenamide with orotic acid and acetone.

Provided is crystalline Tenofovir Alafenamide Napsylate Form I produced by combining Tenofovir Alafenamide with orotic acid and acetone.

Tenofovir Alafenamide Orotate Form II

In some embodiments, provided is a method of producing a composition comprising crystalline Tenofovir Alafenamide Orotate Form II, wherein the method comprise combining Tenofovir Alafenamide Orotate Form I with a solvent. In some embodiments, the method of producing a composition comprising crystalline Tenofovir Alafenamide Orotate Form II comprises combining Tenofovir Alafenamide Orotate Form I with a solvent selected from isopropyl alcohol, tetrahydrofuan, ethyl acetate, toluene, or combination thereof. In some embodiments, the method of producing a composition comprising crystalline Tenofovir Alafenamide Orotate Form II comprises combining Tenofovir Alafenamide Orotate Form I with a solvent wherein the solvent is isopropyl alcohol. In some embodiments, the method of producing a composition comprising crystalline Tenofovir Alafenamide Orotate Form II comprises combining Tenofovir Alafenamide Orotate Form I with a solvent wherein the solvent is tetrahydrofuan. In some embodiments, the method of producing a composition comprising crystalline Tenofovir Alafenamide Orotate Form II comprises combining Tenofovir Alafenamide Orotate Form I with a solvent wherein the solvent is ethyl acetate. In some embodiments, the method of producing a composition comprising crystalline Tenofovir Alafenamide Orotate Form II comprises combining Tenofovir Alafenamide Orotate Form I with a solvent wherein the solvent is toluene.

Provided is crystalline Tenofovir Alafenamide Orotate Form II produced by combining Tenofovir Alafenamide Orotate Form I and a solvent. Provided is crystalline Tenofovir Alafenamide Orotate Form II produced by combining Tenofovir Alafenamide Orotate Form I and a solvent selected from isopropyl alcohol, tetrahydrofuan, ethyl acetate, toluene, or combination thereof. Provided is crystalline Tenofovir Alafenamide Orotate Form II produced by combining Tenofovir Alafenamide Orotate Form I and a solvent wherein the solvent is isopropyl alcohol. Provided is crystalline Tenofovir Alafenamide Orotate Form II produced by combining Tenofovir Alafenamide Orotate Form I and a solvent wherein the solvent is tetrahydrofuan. Provided is crystalline Tenofovir Alafenamide Orotate Form II produced by combining Tenofovir Alafenamide Orotate Form I and a solvent wherein the solvent is ethyl acetate. Provided is crystalline Tenofovir Alafenamide Orotate Form II produced by combining Tenofovir Alafenamide Orotate Form I and a solvent wherein the solvent is toluene.

Tenofovir Alafenamide Orotate Form II

In some embodiments, provided is a method of producing a composition comprising crystalline Tenofovir Alafenamide Orotate Form III, wherein the method comprise combining Tenofovir Alafenamide Orotate Form I with a solvent. In some embodiments, the method of producing a composition comprising crystalline Tenofovir Alafenamide Orotate Form III comprises combining Tenofovir Alafenamide Orotate Form I with a solvent wherein the solvent is water.

Provided is crystalline Tenofovir Alafenamide Orotate Form III produced by combining Tenofovir Alafenamide Orotate Form I and a solvent. Provided is crystalline Tenofovir Alafenamide Orotate Form III produced by combining Tenofovir Alafenamide Orotate Form I and a solvent wherein the solvent is water.

Tenofovir Alafenamide Vanillate

In some embodiments, provided is a method of preparing Tenofovir Alafenamide Vanillate, wherein the method comprises combining tenofovir alafenamide with vanillic acid. In some embodiments, provided is a method of preparing Tenofovir Alafenamide Vanillate wherein the method comprises combining tenofovir alafenamide with vanillic acid and acetone. In some embodiments, provided is a method of preparing Tenofovir Alafenamide Vanillate wherein the method comprises combining tenofovir alafenamide with vanillic acid and acetone at a temperature of about 50° C.

Tenofovir Alafenamide Vanillate

In some embodiments, provided is a method of producing a composition comprising crystalline Tenofovir Alafenamide Vanillate, wherein the method comprise combining Tenofovir Alafenamide with vanillic acid and a solvent. In some embodiments, provided is a method of producing a composition comprising crystalline Tenofovir Alafenamide Vanillate, wherein the method comprise combining Tenofovir Alafenamide with vanillic acid and acetone.

Provided herein is crystalline Tenofovir Alafenamide Vanillate produced by combining Tenofovir Alafenamide with vanillic acid and acetone.

Tenofovir Alafenamide Bis-Xinafoate

In some embodiments, provided is a method of preparing Tenofovir Alafenamide Bis-Xinafoate, wherein the method comprises combining tenofovir alafenamide with 1-hydroxy-2-naphthoic acid and a solvent. In some embodiments, provided is a method of preparing Tenofovir Alafenamide Bis-Xinafoate wherein the method comprises combining tenofovir alafenamide 1-hydroxy-2-naphthoic acid in tetrahydrofuran. In some embodiments, provided is a method of preparing Tenofovir Alafenamide Bis-Xinafoate wherein the method comprises combining tenofovir alafenamide with 1-hydroxy-2-naphthoic acid in tetrahydrofuran and wherein the tetrohydrofuran is evaporated and replaced with a second solvent. In some embodiments, provided is a method of preparing Tenofovir Alafenamide Bis-Xinafoate wherein the method comprises combining tenofovir alafenamide with 1-hydroxy-2-naphthoic acid in tetrahydrofuran and wherein the tetrohydrofuran is evaporated and replaced with dichloromethane. In some embodiments, provided is a method of preparing Tenofovir Alafenamide Bis-Xinafoate wherein the method comprises combining tenofovir alafenamide with 1-hydroxy-2-naphthoic acid in tetrahydrafuran (THF), wherein the tetrahydrafuran is evaporated and replaced with dichloromethane, and wherein the dichloromethane is evaporated.

Tenofovir Alafenamide Bis-Xinafoate

In some embodiments, provided is a method of producing a composition comprising crystalline Tenofovir Alafenamide Bis-Xinafoate, wherein the method comprise combining Tenofovir Alafenamide with 1-hydroxy-2-naphthoic acid and a solvent or a mixture of solvents. In some embodiments, provided is a method of producing a composition comprising crystalline Tenofovir Alafenamide Bis-Xinafoate, wherein the method comprise combining Tenofovir Alafenamide with 1-hydroxy-2-naphthoic acid and THF. In some embodiments, provided is a method of producing a composition comprising crystalline Tenofovir Alafenamide Bis-Xinafoate, wherein the method comprise combining Tenofovir Alafenamide with 1-hydroxy-2-naphthoic acid and THF, followed by evaporation of THF. In some embodiments, provided is a method of producing a composition comprising crystalline Tenofovir Alafenamide Bis-Xinafoate, wherein the method comprise combining Tenofovir Alafenamide with 1-hydroxy-2-naphthoic acid and THF, evaporating the THF, adding dichloromethane, and evaporating the dichlormethane. In some embodiments, provided is a method of producing a composition comprising crystalline Tenofovir Alafenamide Bis-Xinafoate, wherein the method comprise a first step of combining Tenofovir Alafenamide with 1-hydroxy-2-naphthoic acid and THF, a second step of evaporating the THF, a third step of adding dichloromethane, and a fourth step of evaporating the dichlormethane. In some embodiments, provided is a method of producing a composition comprising crystalline Tenofovir Alafenamide Bis-Xinafoate, wherein the method comprises creating a tenofovir alafenamide bis-xinafoate seed crystal by combining tenofovir alafenamide with 1-hydroxy-2-naphthoic acid in THF, wherein the tenofovir alafenamide bis-xinafoate seed crystal is then use to seed a solution of 1-hydroxy-2-naphthoic acid in a solvent selected from methanol, ethanol, acetone, isopropanol, methyl isobutyl ketone (MIBK), ethyl acetate, isopropyl acetate, toluene, or a mixture thereof. In some embodiments, provided is a method of producing a composition comprising crystalline Tenofovir Alafenamide Bis-Xinafoate, wherein the method comprise combining Tenofovir Alafenamide with 1-hydroxy naphthoic acid and acetone. In some embodiments, provided is a method of producing a composition comprising crystalline Tenofovir Alafenamide Bis-Xinafoate, wherein the method comprise combining Tenofovir Alafenamide with 1-hydroxy-2-naphthoic acid and acetone, followed by evaporation of the acetone.

Uses in Manufacturing of Drug Product

Provided is also a use of the crystalline forms described herein in the manufacture of a drug product. The one or more of the crystalline forms described herein (e.g., the compounds described herein) may be used in the manufacturing process to produce the drug product. The one or more of the crystalline forms described herein (e.g., the compounds described herein) may be used as an intermediate in the manufacturing process to produce the drug product.

In certain embodiments, crystalline salts and/or co-crystals of tenofovir alafenamide are used in the manufacture of an active pharmaceutical ingredient. In certain embodiments, Tenofovir Alafenamide Hemipamoate Form I is used in the manufacture of an active pharmaceutical ingredient. In certain embodiments, Tenofovir Alafenamide Hemipamoate Form II is used in the manufacture of an active pharmaceutical ingredient. In certain embodiments, Tenofovir Alafenamide Sebacate Form I is used in the manufacture of an active pharmaceutical ingredient. In certain embodiments, Tenofovir Alafenamide Napsylate Form I is used in the manufacture of an active pharmaceutical ingredient. In certain embodiments, Tenofovir Alafenamide Orotate Form I is used in the manufacture of an active pharmaceutical ingredient. In certain embodiments, Tenofovir Alafenamide Orotate Form II is used in the manufacture of an active pharmaceutical ingredient. In certain embodiments, Tenofovir Alafenamide Orotate Form III is used in the manufacture of an active pharmaceutical ingredient.

In certain embodiments, Tenofovir Alafenamide Vanillate is used in the manufacture of an active pharmaceutical ingredient. In certain embodiments, Tenofovir Alafenamide Bis-Xinafoate is used in the manufacture of an active pharmaceutical ingredient.

Articles of Manufacture and Kits

Compositions comprising one or more of the crystalline forms described herein (e.g., a compound described herein) and formulated in one or more pharmaceutically acceptable excipients or other ingredients can be prepared, placed in an appropriate container, and labeled for treatment of an indicated condition. Accordingly, there also is contemplated an article of manufacture, such as a container comprising a dosage form of one or more of the crystalline forms described herein and a label containing instructions for use of the compound(s).

In some embodiments, the article of manufacture is a container comprising a dosage form of one or more of the crystalline forms described herein, and one or more pharmaceutically acceptable excipients or other ingredients. In some embodiments of the articles of manufacture described herein, the dosage form is a solution.

Kits also are contemplated. For example, a kit can comprise a dosage form of a pharmaceutical composition and a package insert containing instructions for use of the composition in treatment of a medical condition. In another embodiment a kit may comprise multiple individual dosage forms, each comprising a therapeutically effective amount of a compound as described herein, and instructions for their administration to a human in need thereof. Each of the individual dosage forms may comprise a therapeutically effective amount of a compound as described herein in combination with at least one pharmaceutically effective excipient. The individual dosage forms may be in the form of, as examples, a solution, a tablet, a pill, a capsule, a sachet, a sublingual medicament, a lyophilized powder, a spray-dried powder, or a liquid composition for oral, parenteral, or topical administration. The instructions for use in the kit may be for treating an HIV virus infection. The instructions may be directed to any of the viral infections and methods described herein. The instructions may be for prophylaxis or the treatment of an existing viral infection.

In certain embodiments, the crystalline or salt forms described herein may potentially exhibit improved properties. For example, in certain embodiments, the crystalline or salt forms described herein may potentially exhibit improved stability. Such improved stability could have a potentially beneficial impact on the manufacture of the compounds described here, such as for example offering the ability to store process intermediate for extended periods of time. Improved stability could also potentially benefit a composition or pharmaceutical composition of the compounds described herein. In certain embodiments, the crystalline or salt described herein may also potentially result in improved yield of the compounds described herein, or potentially result in an improvement of the quality of the compounds described herein. In certain embodiments, the crystalline, salt and solvate forms described herein may also exhibit improved pharmacokinetic properties and/or potentially improved bioavailability.

Methods

Tenofovir Alafenamide Hemipamoate Form I

Tenofovir Alafenamide (about 1 g) was mixed with pamoic acid (about 0.4 g) and tetrahydrofuan (about 10 mL) at about 50 to 60° C. The solution was put in a glass vial with an open lid and allowed to evaporate. The sample was further dried in an oven. The solid was mixed with acetonitrile. Tenofovir Alafenamide Hemipamoate Form I was isolated and characterized as discussed below. It was also found that acetonitrile can be replaced with ethanol, acetone, isopropyl acetate, methyl ethyl ketone, tetrahydrofuan, or toluene to form Tenofovir Alafenamide Hemipamoate Form I.

In another method for producing Tenofovir Alafenamide Hemipamoate Form I, tenofovir alafenamide (about 10 g), pamoic acid (about 4 g) and tetrahydrofuan (about 150 mL) were combined at about 70° C. The solution was filtered and evaporated. The solids were dissolved in acetone (about 100 mL) at about 40° C. and cooled to about room temperature. Tenofovir Alafenamide Hemipamoate Form I seeds were added. Tenofovir Alafenamide Hemipamoate Form I was isolated and characterized as discussed below.

Tenofovir Alafenamide Hemipamoate Form II

Tenofovir Alafenamide Hemipamoate Form I (about 100 mg) was mixed with dichloromethane (about 1 mL). Tenofovir Alafenamide Hemipamoate Form II was isolated and characterized as discussed below.

Tenofovir Alafenamide Sebacate Form I

Tenofovir alafenamide (about 1 g) was mixed with sebacic acid (about 0.4 g) and acetone (about 10 mL). The solution was put in a glass vial with an open lid and allowed to evaporate. Tenofovir Alafenamide Sebacate Form I was isolated and characterized as discussed below.

Tenofovir Alafenamide Napsylate Form I

Tenofovir Alafenamide (about 1 g) was mixed with 2-naphthalenesulfonic acid (about 0.4 g) and acetone (about 10 mL). The solution was put in a glass vial with an open lid and allowed to evaporate. Tenofovir Alafenamide Napsylate Form I was isolated and characterized as discussed below.

Tenofovir Alafenamide Orotate Form I

Tenofovir Alafenamide (about 1 g) was mixed with orotic acid (about 0.3 g) and acetone (about 10 mL). The solution was put in a glass vial with an open lid and allowed to evaporate. Tenofovir Alafenamide Orotate Form I was isolated and characterized as discussed below.

Tenofovir Alafenamide Orotate Form II

Tenofovir Alafenamide Orotate Form I was mixed with isopropyl acetate at about room temperature for not less than 12 hours. Tenofovir Alafenamide Orotate Form II was isolated and characterized as discussed below. It was also found that isopropyl acetate can be replaced with tetrahydrofuan, ethyl acetate, or toluene to form Tenofovir Alafenamide Orotate Form II.

Tenofovir Alafenamide Orotate Form III

Tenofovir Alafenamide Orotate Form I was mixed with water at about room temperature for not less than 12 hours. Tenofovir Alafenamide Orotate Form III was isolated and characterized as discussed below.

Tenofovir Alafenamide Vanillate 1 g tenofovir alafenamide free base was dissolved in 10 mL acetone at 50° C., filtered and mixed with 0.35 g (1 equivalent) vanillic acid to obtain a solution. The solution was stirred at about 21° C. overnight to form a slurry. The slurry was isolated by filtration and dried at 50° C. under vacuum.

Tenofovir Alafenamide Bis-xinafoate 4 g of tenofovir alafenamide free base was mixed with 1.5 eq 1-hydroxy-2-naphthoic acid in 10 mL THF to form a solution, which was dried to a foam in a rotovapor at about 50° C. 200 mg to 500 mg of the resulted solids were stirred in 1 mL of DCM at about 21° C. The sample was evaporated with its lid open and became thick syrup. The syrup was further evaporated at 57° C. and it crystallized during a period of 16 hours. This crystalline material was used to seed solutions of tenofovir alafenamide with 1.5 eq 1-hydroxy-2-naphthoic acid in solvents such as methanol, ethanol, acetone, isopropanol, MIBK, ethyl acetate, isopropyl acetate, toluene, and they all crystallized as the same form.

Alternatively, 4 g of tenofovir alafenamide free base was dissolved in 40 mL acetone at 50° C., filtered, charged with 3.16 g 1-hydroxy-naphthoic acid (2 eq.) to form a solution. The solution was dried in a rotary evaporator at 50° C. to a foam, and redissolved in 40 mL IPAc(isopropyl acetate). The solution was seeded with crystals of tenofovir alafenamide bis-xinafoate, sonicated, and a thick slurry formed soon afterwards. The slurry was diluted with 16 mL IPAc, filtered, and dried in the vacuum oven at 50° C. for three days.

The crystalline forms of the present invention were characterized by various analytical techniques, including X-ray powder diffraction (XRPD), differential scanning calorimetry (DSC), and thermogravimetric analysis (TGA), using the procedures described below.

X-Ray Powder Diffraction (XRPD): XRPD patterns were collected on a PANanalytical XPERT-PRO diffractometer at ambient conditions under the following experimental settings: 45 KV, 40 mA, Kal=1.5406 Å, scan range 2 to 40°, step size 0.0084 or 0.0167°, measurement time: 5 min.

The XRPD pattern for Tenofovir Alafenamide Hemipamoate Form I is represented in FIG. 1.

The XRPD pattern for Tenofovir Alafenamide Hemipamoate Form II is represented in FIG. 3.

The XRPD pattern for Tenofovir Alafenamide Sebacate Form I is represented in FIG. 5.

The XRPD pattern for Tenofovir Alafenamide Napsylate Form I is represented in FIG. 7.

The XRPD pattern for Tenofovir Alafenamide Orotate Form I is represented in FIG. 9.

The XRPD pattern for Tenofovir Alafenamide Orotate Form II is represented in FIG. 11.

The XRPD pattern for Tenofovir Alafenamide Orotate Form III is represented in FIG. 13.

The XRPD pattern for Tenofovir Alafenamide Vanillate is represented in FIG. 15.

The XRPD pattern for Tenofovir Alafenamide Bis-xinafoate is represented in FIG. 17.

Differential scanning calorimetry (DSC): DSC thermograms were collected on a TA Instruments Q2000 system equipped with a 50 position auto-sampler. The calibration for energy and temperature was carried out using certified indium. Typically 1-5 mg of each sample, in a pin-holed aluminium pan, was heated at 10° C./min from 25° C. to 300° C. A purge of dry nitrogen at 50 mL/min was maintained over the sample throughout the measurement. The onset of the melting endotherm was reported as the melting point.

The DSC for Tenofovir Alafenamide Hemipamoate Form I is represented in FIG. 2.

The DSC for Tenofovir Alafenamide Hemipamoate Form II is represented in FIG. 4.

The DSC for Tenofovir Alafenamide Sebacate Form I is represented in FIG. 6.

The DSC for Tenofovir Alafenamide Napsylate Form I is represented in FIG. 8.

The DSC for Tenofovir Alafenamide Orotate Form I is represented in FIG. 10.

The DSC for Tenofovir Alafenamide Orotate Form II is represented in FIG. 12.

The DSC for Tenofovir Alafenamide Orotate Form III is represented in FIG. 14.

The DSC for Tenofovir Alafenamide Vanillate is represented in FIG. 16.

The DSC for Tenofovir Alafenamide Bis-Xinafoate is represented in FIG. 18.

Solubility Screen

In a vial that contains pre-weighed amount of solid, deionized water was added in small increments at approximately 22° C. The solid/liquid mixture was agitated by a vortex mixer and held at room temperature. Continued to add deionized water and repeated the mixing until the solid was fully dissolved. The solubilities of various salts were measured by the preceding procedure and values are reflected in Table 2 below.

TABLE 2

| Salt Form | Solubility |
| --- | --- |
| TAF Hemipamoate | 0.15 mg/mL |
| TAF Sebacate | 0.7 mg/mL |
| TAF Napsylate | 7 mg/mL |
| TAF Orotate | 1.7 mg/mL |
| TAF Vanillate | 1.6 mg/mL |
| TAF Bis-xinafoate | 0.2 mg/mL |
| TAF Hemifumarate (Control) | 20 mg/mL |

The lower solubility of the salt forms (compared with Hemifumarate) provides extended duration of release corresponding to a long acting formulation.

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed:

1. Crystalline Tenofovir Alafenamide Napsylate Form I, characterized by an X-ray powder diffraction (XRPD) pattern having peaks at about 3.9°, 7.8°, 13.6°, 15.3°, and 19.2° 2-θ±0.2° 2-θ.

2. The crystalline form of claim 1, wherein the X-ray powder diffraction (XRPD) pattern has further peaks at about 19.4°, 19.8°, 20.6°, 23.8°, and 27.2° 2-θ±0.2° 2-θ.

3. The crystalline form of claim 2, wherein the X-ray powder diffraction (XRPD) pattern has further peaks at about 9.8°, 13.2°, 15.5°, 16.5°, 17.8°, 23.0°, 24.1°, and 26.0° 2-θ±0.2° 2-θ.

4. The crystalline form of claim 1, characterized by an X-ray powder diffraction (XRPD) pattern as set forth in FIG. 7.

5. The crystalline form of claim 1, characterized by a differential scanning calorimetry (DSC) pattern as set forth in FIG. 8.

6. A pharmaceutical composition comprising a therapeutically effective amount of the crystalline Tenofovir Alafenamide Napsylate of claim 1 and a pharmaceutically acceptable excipient.

7. The pharmaceutical composition of claim 6, further comprising one to three additional therapeutic agents.

8. The pharmaceutical composition of claim 7, wherein the additional therapeutic agents are each active against HIV.

9. The pharmaceutical composition of claim 6, wherein the pharmaceutical composition is in a unit dosage form.

10. The pharmaceutical composition of claim 9, wherein the unit dosage form is a subcutaneous injection.

11. A method for treating a virus infection in a human, the method comprising administering to a human in need thereof a therapeutically effective amount of the crystalline Tenofovir Alafenamide Napsylate of claim 1.

12. The method of claim 11 wherein the virus infection is caused by HIV.

13. The pharmaceutical composition of claim 9, wherein the unit dosage form is an injection.

14. The pharmaceutical composition of claim 9, wherein the unit dosage form is an intramuscular injection.

15. The pharmaceutical composition of claim 9, wherein the crystalline Tenofovir Alafenamide Napsylate is in a suspension.

16. The method of claim 11, wherein the crystalline Tenofovir Alafenamide Napsylate is administered by injection.

17. The method of claim 11, wherein the crystalline Tenofovir Alafenamide Napsylate is administered by intramuscular injection.

18. The method of claim 11, wherein the crystalline Tenofovir Alafenamide Napsylate is administered by subcutaneous injection.

19. The method of claim 18, wherein the crystalline Tenofovir Alafenamide Napsylate is in a suspension.

20. The method of claim 12, wherein the crystalline Tenofovir Alafenamide Napsylate is in a long-acting formulation.

21. The method of claim 20, wherein the long-acting formulation is active for at least 30 days.

22. The method of claim 21, wherein the long-acting formulation maintains a concentration minimum (Cmin) above the efficacious level for HIV treatment.

* * * * *